(12) United States Patent
Fischer et al.

(10) Patent No.: US 7,105,553 B2
(45) Date of Patent: Sep. 12, 2006

(54) THIAZOLYL AMIDE DERIVATIVES

(75) Inventors: Rüdiger Fischer, Pulheim (DE);
Gerald Kleymann, Bad Salzuflen (DE);
Ulrich Betz, Wuppertal (DE); Judith Baumeister, Wuppertal (DE);
Wolfgang Bender, Wuppertal (DE);
Peter Eckenberg, Wuppertal (DE);
Gabriele Handke, Wülfrath (DE);
Martin Hendrix, Odenthal (DE);
Kerstin Henninger, Wuppertal (DE);
Axel Jensen, Velbert (DE); Jörg Keldenich, Wuppertal (DE); Udo Schneider, Leverkusen (DE); Olaf Weber, Woodbridge, CT (US)

(73) Assignee: Bayer Aktiengesellschaft, Leverkusen (DE)

( * ) Notice: Subject to any disclaimer, the term of this patent is extended or adjusted under 35 U.S.C. 154(b) by 563 days.

(21) Appl. No.: 10/168,197

(22) PCT Filed: Dec. 12, 2000

(86) PCT No.: PCT/EP00/12564

§ 371 (c)(1),
(2), (4) Date: Nov. 12, 2002

(87) PCT Pub. No.: WO01/47904

PCT Pub. Date: Jul. 5, 2001

(65) Prior Publication Data

US 2004/0006076 A1 Jan. 8, 2004

(30) Foreign Application Priority Data

Dec. 23, 1999 (DE) .......................................... 199 62 532

(51) Int. Cl.
*A61K 31/426* (2006.01)
*C07D 277/54* (2006.01)

(52) U.S. Cl. ...................................... 514/369; 548/185

(58) Field of Classification Search ................. 548/185; 514/369
See application file for complete search history.

(56) References Cited

U.S. PATENT DOCUMENTS

| 3,658,830 A | 4/1972 | Pilgram et al. .......... 260/306.8 |
| 3,717,651 A | 2/1973 | Pilgram et al. .......... 260/306.8 |
| 3,847,588 A | 11/1974 | Pilgram et al. ................. 71/90 |

FOREIGN PATENT DOCUMENTS

| EP | 0860700 | 8/1998 |
| GB | 1323045 | 7/1973 |
| GB | 2311068 | 9/1997 |
| GB | 2311069 | 9/1997 |
| WO | 9724343 | 7/1997 |
| WO | 9736006 | 10/1997 |
| WO | 9937291 | 7/1999 |
| WO | 9942455 | 8/1999 |
| WO | 9947507 | 9/1999 |
| WO | 0053591 | 9/2000 |

OTHER PUBLICATIONS

Crute, J. et al., Inhibition of Herpes Simplex Virus Type 1 Helicase–Primase by (Dichloroanilino)purines and—pyrimidines, J. Med. Chem., (38(10): 1820–1825 (1995).
Matthews, J., et al., The structrure and function of the HSV DNA replication proteins: defining novel antiviral targets, Antiviral Research, 20: 89–114 (1993).
Hantzsch, A., Über Die Oxy–thiazole oder Thiazolone, Chem. Ber., 60:2537–2545 (1927).
Artico, M., et al., Aromatic hydrazides as specific inhibitors of bovine serum amine oxidase , Eur J. Med. Chem., 27:219–228 (1992).
Bartmann, E., et al., Synthesis of α, α–difluoronitriles from acyl cyanides, J. Fluorine Chem., 61:117–122 (1993).
Ziegler, C., Kuhl, E. K., and Spragus, J. M., "2–Aminothiazolesulfonamides", J. Org. Chem., Am. Chem. Soc., 25: 1454–1455 (Aug. 1960).

*Primary Examiner*—Laura L. Stockton

(57) ABSTRACT

The present invention relates to novel compounds, to a process for their preparation and to their use as medicaments, in particular as antiviral medicaments.

19 Claims, No Drawings

THIAZOLYL AMIDE DERIVATIVES

The present invention relates to novel compounds, namely thiazolyl amide derivatives, to processes for their preparation and to their use as medicaments, in particular as antiviral medicaments.

2-Aminothiazole-5-sulphonamides are known from the publication C. Ziegler et al., J. Org. Chem. 25, 1960, 1454–1455. Moreover, the German Offenlegungsschrift 2101640 describes N-thiazol-2-yl-amides and -ureas having herbicidal action.

WO97/24343 relates to phenylthiazole derivatives having anti-herpes-virus properties.

WO99/42455 likewise relates to phenylthiazole derivatives having anti-herpes-virus properties.

WO99/47507 relates to 1,3,4-thiadiazole derivatives having anti-herpes-virus properties.

The present invention relates to novel compounds which are thiazolyl amide derivatives of the general formula (I):

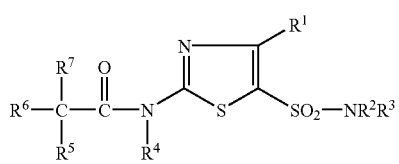

in which $R^1$ represents hydrogen, halogen, $(C_1–C_6)$-alkyl, $(C_1–C_6)$-alkoxy, amino-$(C_1–C_6)$-alkyl or halogeno-$(C_1–C_6)$-alkyl, $R^2$ and $R^3$ are identical or different and represent hydrogen, $(C_1–C_6)$-alkoxy, $(C_3–C_8)$-cycloalkyl or biphenylaminocarbonyl, or represent $(C_1–C_6)$-alkyl which is optionally substituted by 1 to 3 substituents selected from the group consisting of $(C_3–C_6)$-cycloalkyl, $(C_1–C_6)$-alkoxy, halogen, hydroxyl, amino, tri-$(C_1–C_6)$-alkylsilyloxy, radicals of the formula

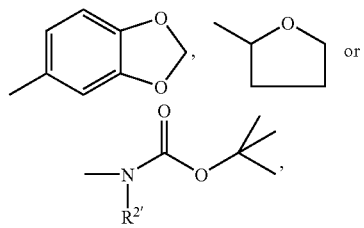

in which $R^{2'}$ represents hydrogen or $(C_1–C_4)$-alkyl, a 5- or 6-membered aromatic heterocycle having up to 3 heteroatoms from the group consisting of S, N and O, where a nitrogen-containing heterocycle may also be attached via the nitrogen atom, a 3- to 8-membered saturated or unsaturated nonaromatic heterocycle having up to 3 heteroatoms from the group consisting of S, N and O, which may optionally be attached via a nitrogen atom, and $(C_6–C_{10})$-aryl which for its part may be substituted by hydroxyl or $(C_1–C_6)$-alkoxy, or represent a group of the formula

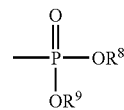

in which $R^8$ and $R^9$ are identical to or different from one another and represent hydrogen and $(C_1–C_4)$-alkyl, or represent a group of the formula

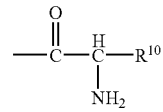

in which $R^{10}$ is the side-group of a naturally occurring α-amino acid, or represent a group of the formula

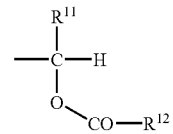

in which $R^{11}$ represents $(C_1–C_4)$-alkyl and $R^{12}$ represents hydrogen, $(C_1–C_4)$-alkyl or represents a group of the formula

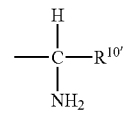

in which $R^{10'}$ is the side-group of a naturally occurring α-amino acid, or $R^2$ and $R^3$ together with the nitrogen atom form a 5- or 6-membered saturated heterocycle which may optionally contain an oxygen atom, $R^4$ represents hydrogen, $(C_1–C_6)$-acyl, $(C_2–C_6)$-alkenyl, $(C_3–C_8)$-cycloalkyl, or $R^4$ represents $(C_1–C_6)$-alkyl which may optionally be substituted by 1 to 3 substituents selected from the group consisting of halogen, hydroxyl, $(C_3–C_8)$-cycloalkyl, $(C_1–C_6)$-acyl, $(C_1–C_6)$-alkoxy, carboxyl,

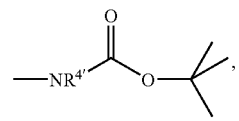

in which $R^{4'}$ represents hydrogen, —$(OCH_2CH_2)_n$OCH$_2$CH$_3$, in which n is 0 or 1, phenoxy, $(C_6–C_{10})$-aryl and —$NR^{13}R^{14}$, in which $R^{13}$ and $R^{14}$ are identical or different and represent hydrogen, $(C_1–C_6)$-acyl, $(C_1–C_6)$-alkyl, carbamoyl, mono- or di-$(C_1–C_6)$-alkylamino-$(C_1–C_6)$-alkyl, mono- or di-$(C_1–C_6)$-alkylaminocarbonyl, $(C_6–C_{10})$-aryl or $(C_1–C_6)$-alkoxycarbonyl, or $R^{13}$ and $R^{14}$ together with the nitrogen atom form a 5- or 6-membered saturated heterocycle which may optionally contain a further heteroatom from the group consisting of S and O or a radical of the formula —NR$^{15}$, and which may be substituted by oxo,
in which
R$^{15}$ represents hydrogen or (C$_1$–C$_4$)-alkyl, or
R$^4$ represents (C$_1$–C$_6$)-alkyl which is substituted by a 5- or 6-membered aromatic, optionally benzo-fused heterocycle having up to 3 heteroatoms from the group consisting of S, N and O, where a nitrogen-containing heterocycle may also be attached via the nitrogen atom, or which is substituted by radicals of the formulae

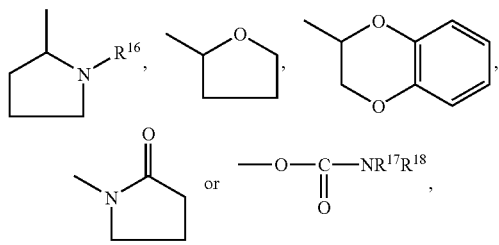

in which
R$^{16}$ represents hydrogen or (C$_1$–C$_6$)-alkyl,
R$^{17}$ and R$^{18}$ are identical or different and represent hydrogen, (C$_1$–C$_6$)-alkyl or (C$_6$–C$_{10}$)-aryl, where abovementioned (C$_1$–C$_6$)-alkyl and (C$_6$–C$_{10}$)-aryl may optionally be substituted by 1 to 3 substituents selected from the group consisting of hydroxyl, (C$_1$–C$_6$)-alkoxy and halogen,
R$^5$ represents hydrogen, (C$_1$–C$_6$)-alkyl, halogen, amino, mono- or di-(C$_1$–C$_6$)-alkylamino or represents (C$_1$–C$_6$)-alkanoylamino,
R$^6$ represents phenyl which may optionally be substituted by one to three substituents selected from the group consisting of
halogen,
(C$_6$–C$_{10}$)-aryl which may optionally be substituted by 1 to 3 substituents selected from the group consisting of (C$_1$–C$_6$)-alkanoyl, (C$_1$–C$_6$)-alkoxy, (C$_1$–C$_6$)-alkyl, halogen, (C$_1$–C$_6$)-alkoxycarbonyl, nitro, halogeno-(C$_1$–C$_6$)-alkyl, halogeno-(C$_1$–C$_6$)-alkoxy, amino, (C$_1$–C$_6$)-alkylthio, hydroxyl, carboxyl, carbamoyl, mono- or di-(C$_1$–C$_6$)-alkylaminocarbonyl, mono- or di-(C$_1$–C$_6$)-alkanoylamino, (C$_1$–C$_6$)-alkoxycarbonylamino, (C$_1$–C$_6$)-alkylsulphoxy, (C$_1$–C$_6$)-alkylsulphonyl, tri-(C$_1$–C$_6$)-alkylsilyloxy, a 3- to 8-membered saturated or unsaturated non-aromatic mono- or bicyclic heterocycle having up to 3 heteroatoms from the group consisting of S, N and O, which may optionally be attached via a nitrogen atom, and/or cyano,
(C$_1$–C$_6$)-alkoxy,
(C$_1$–C$_6$)-alkoxycarbonyl,
(C$_1$–C$_6$)-alkylthio,
hydroxyl,
carboxyl,
partially fluorinated (C$_1$–C$_6$)-alkoxy having up to 6 fluorine atoms,
(C$_1$–C$_6$)-alkyl which is optionally substituted by a radical of the formula

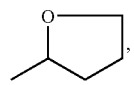

a 5- or 6-membered aromatic heterocycle having up to 3 heteroatoms from the group consisting of S, N and O which may optionally be attached via a nitrogen atom and which may optionally be substituted by 1 to 3 substituents selected from the group consisting of (C$_1$–C$_6$)-alkanoyl, (C$_1$–C$_6$)-alkoxy, (C$_1$–C$_6$)-alkyl, halogen, (C$_1$–C$_6$)-alkoxycarbonyl, nitro, halogeno-(C$_1$–C$_6$)-alkyl, halogeno-(C$_1$–C$_6$)-alkoxy, amino, (C$_1$–C$_6$)-alkylthio, hydroxyl, carboxyl, carbamoyl, aminocarbonyl, mono- or di-(C$_1$–C$_6$)-alkylaminocarbonyl, mono- or di-(C$_1$–C$_6$)-alkanoylamino, (C$_1$–C$_6$)-alkoxycarbonylamino, (C$_1$–C$_6$)-alkylsulphoxy, (C$_1$–C$_6$)-alkylsuphonyl, a 3- to 8-membered saturated or unsaturated nonaromatic mono- or bicyclic heterocycle having up to 3 heteroatoms from the group consisting of S, N and O which may optionally be attached via a nitrogen atom, and/or cyano,
a 3- to 8-membered saturated or unsaturated nonaromatic mono- or bicyclic heterocycle having up to 3 heteroatoms from the group consisting of S, N and O, which may optionally be attached via a nitrogen atom and which may optionally be substituted by 1 to 3 substituents selected from the group consisting of oxo, halogen, hydroxyl, (C$_1$–C$_6$)-alkoxycarbonyl, (C$_1$–C$_6$)-alkoxycarbonylamino, (C$_1$–C$_6$)-alkyl, halogeno-(C$_1$–C$_6$)-alkyl and hydroxy-(C$_1$–C$_6$)-alkyl, (C$_2$–C$_6$)-alkenyl
and groups of the formulae
—OR$^{19}$,
—NR$^{20}$R$^{21}$ or —CO—NR$^{22}$R$^{23}$,
carbazole, dibenzofuran or dibenzothiophene,
xanthene or 9,10-dihydroacridine,
in which R$^{19}$ is phenyl which for its part is optionally substituted by a group of the formula —NR$^{24}$R$^{25}$
in which
R$^{24}$ and R$^{25}$ are identical or different and represent hydrogen, (C$_1$–C$_6$)-alkyl or (C$_1$–C$_6$)-acyl, or
R$^{19}$ represents (C$_1$–C$_6$)-alkyl which is optionally mono- to trisubstituted by hydroxyl and/or halogen,
R$^{20}$ and R$^{21}$ are identical or different and represent hydrogen, carbamoyl, mono- or di-(C$_1$–C$_6$)-alkylaminocarbonyl, phenyl, (C$_1$–C$_6$)-acyl or (C$_1$–C$_6$)-alkyl,
where abovementioned (C$_1$–C$_6$)-alkyl is optionally substituted by (C$_1$–C$_6$)-alkoxy, (C$_1$–C$_6$)-acyl, by phenyl or by a 5- or 6-membered aromatic heterocycle having up to 3 heteroatoms from the group consisting of S, N and O,
where abovementioned phenyl and abovementioned aromatic heterocycle are optionally mono- to trisubstituted by identical or different substituents from the group consisting of halogen and hydroxyl, and
R$^{22}$ and R$^{23}$ are identical or different and represent hydrogen or (C$_1$–C$_6$)-alkyl,
and R$^7$ may have the meaning of R$^5$ and may be identical to or different from R$^5$,
and their salts.
Physiologically acceptable salts of the compounds according to the invention can be, for example, salts of the substances according to the invention with mineral acids, carboxylic acids or sulphonic acids. Particular preference is given, for example, to salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid, or benzoic acid.

Salts which may furthermore be mentioned are salts with customary bases, such as, for example, alkali metal salts (for example sodium or potassium salts), alkaline earth metal salts (for example calcium or magnesium salts) or ammonium salts, derived from ammonia or organic amines, such as, for example, diethylamine, triethylamine, ethyldiisopropylamine, procaine, dibenzylamine, N-methylmorpholine, dihydroabietylamine, 1-ephenamine or methylpiperidine.

Depending on the substitution pattern, the compounds according to the invention can exist in stereoisomeric forms which either behave as image and mirror image (enantiomers), or which do not behave as image and mirror image (diastereomers). The invention relates both to the enantiomers or diastereomers and their respective mixtures. Like the diastereomers, the racemic forms can be separated into the stereoisomerically uniform components in a known manner.

The scope of the invention includes those compounds which are only converted into the actual active compounds of the formula (I) once inside the body (so-called prodrugs).

$(C_1-C_6)$-Alkyl advantageously represents a straight-chain or branched alkyl radical having from 1 to 6 carbon atoms. Preference is given to a straight-chain or branched alkyl radical having 1 to 4 carbon atoms $(C_1-C_4)$. Examples which may be mentioned are:

methyl, ethyl, n-propyl, isopropyl, n-butyl, sec-butyl, tert-butyl, n-pentyl and n-hexyl. Particular preference is given to a straight-chain or branched alkyl radical having 1 to 3 carbon atoms ($(C_1-C_3)$-alkyl).

Halogeno-$(C_1-C_6)$-alkyl advantageously represents a $(C_1-C_6)$-alkyl group which can be defined as above and which has 1 to 3 halogen atoms, namely F, Cl, Br and/or I, preferably chlorine or fluorine, as substituents; examples which may be mentioned are trifluoromethyl, fluoromethyl, etc.

Hydroxy-$(C_1-C_6)$-alkyl advantageously represents a $(C_1-C_6)$-alkyl group which can be defined as above and which has 1 to 3 hydroxyl groups as substituents; examples which may be mentioned are hydroxymethyl etc.

$(C_1-C_6)$-Alkenyl in the context of the invention advantageously represents a straight-chain or branched alkenyl radical having 2 to 6 carbon atoms. Examples which may be mentioned are: ethenyl, n-prop-2-en-1-yl and n-but-2-en-1-yl. Preference is given to a straight-chain or branched alkenyl radical having 2 to 4 carbon atoms.

$(C_1-C_6)$-Alkoxy advantageously represents a straight-chain or branched alkoxy radical having 1 to 6 carbon atoms. Preference is given to a straight-chain or branched alkoxy radical having 1 to 4 carbon atoms $(C_1-C_4)$. Examples which may be mentioned are: methoxy, ethoxy, n-propoxy, isopropoxy, tert-butoxy, n-pentoxy and n-hexoxy. Particular preference is given to a straight-chain or branched alkoxy radical having 1 to 3 carbon atoms-$(C_1-C_3)$.

Halogeno-$(C_1-C_6)$-alkoxy advantageously represents mono- or polyhalogenated $(C_1-C_6)$-alkoxy. With respect to the $(C_1-C_6)$-alkoxy moiety and the definition of halogen, reference is made to the above definition. Halogeno-$(C_1-C_6)$-alkoxy includes, for example, partially mono- or polychlorinated and/or -fluorinated or -perfluorinated $(C_1-C_6)$-alkoxy, such as trifluoromethoxy, fluoromethoxy, chloromethoxy, pentafluoroethoxy, trifluoromethylmethoxy, etc.

Partially fluorinated $(C_1-C_6)$-alkoxy having up to 6 fluorine atoms advantageously represents a straight-chain or branched alkoxy radical having 1 to 6 carbon atoms which may be substituted by 1 to 6, preferably 1 to 4, more preferably 1 to 3, fluorine atoms. Preference is given to a straight-chain or branched alkoxy radical having 1 to 4 carbon atoms and 1 to 4 fluorine atoms. Examples which may be mentioned are: methoxy, ethoxy, n-propoxy, isopropoxy, tert-butoxy, n-pentoxy and n-hexoxy, which in each case have 1 to 4 fluorine atoms. Particular preference is given to (1,3-difluoroprop-2-yl)-oxy and 1,1,2,2-tetrafluorethoxy.

$(C_1-C_6)$-Alkylthio advantageously represents a straight-chain or branched alkylthio radical having 1 to 6 carbon atoms. Preference is given to a straight-chain or branched alkylthio radical having 1 to 4 carbon atoms $(C_1-C_4)$. Examples which may be mentioned are: methylthio, ethylthio, n-propylthio, isopropylthio, tert-butylthio, n-pentylthio and n-hexylthio. Particular preference is given to a straight-chain or branched alkylthio radical having 1 to 3 carbon atoms $(C_1-C_3)$-alkylthio.

$(C_1-C_6)$-Alkoxycarbonyl advantageously represents a straight-chain or branched alkoxycarbonyl radical having 1 to 6 carbon atoms. Preference is given to a straight-chain or branched alkoxycarbonyl radical having 1 to 4 carbon atoms $(C_1-C_4)$. Examples which may be mentioned are: methoxycarbonyl, ethoxycarbonyl, n-propoxycarbonyl, isopropoxycarbonyl and tert-butoxycarbonyl. Particular preference is given to a straight-chain or branched alkoxycarbonyl radical having 1 to 4 carbon atoms $(C_1-C_4)$.

Mono- or di-$(C_1-C_6)$-alkylaminocarbonyl in the context of the invention advantageously represents a carbamoyl group ($H_2N-CO-$), in which one or both hydrogen atoms are replaced by a $(C_1-C_6)$-alkyl group. With respect to the definition of the $(C_1-C_6)$-alkyl group, reference is made to the above explanation of $(C_1-C_6)$-alkyl. Examples which may be mentioned are methylaminocarbonyl, dimethylamino, etc.

Mono- or di-$(C_1-C_6)$-acylamino in the context of the invention advantageously represents an amino group ($H_2N-$) in which one or both hydrogen atoms are replaced by a $(C_1-C_6)$-acyl group. With respect to the definition of the $(C_1-C_6)$-acyl group, reference is made to the above explanation of $(C_1-C_6)$-acyl. An example which may be mentioned is $(C_1-C_6)$-alkanoyl, as mentioned in the definition of $(C_1-C_6)$-acyl.

$(C_1-C_6)$-Alkylsulphoxy advantageously represents a $(C_1-C_6)$-alkyl-$S(=O)-$ group, where, with respect to the $(C_1-C_6)$-alkyl group, reference can be made to the relevant definition above.

$(C_1-C_6)$-Alkylsulphonyl advantageously represents a $(C_1-C_6)$-alkyl-$SO_2$ group where, with respect to the $(C_1-C_6)$-alkyl group, reference can be made to the relevant definition above.

$(C_6-C_{10})$-Aryl generally represents an aromatic radical having 6 to 10 carbon atoms. Preferred aryl radicals are phenyl and naphthyl.

$(C_1-C_6)$-Acyl in the context of the invention advantageously represents a straight-chain or branched acyl radical having 1 to 6 carbon atoms. Examples which may be mentioned are: formyl, acetyl, ethanoyl, propanoyl, isopropanoyl, butanoyl, isobutanoyl and pentanoyl. Preference is given to a straight-chain or branched acyl radical having 1 to 4 carbon atoms. Particular preference is given to acetyl and ethanoyl.

$(C_3–C_8)$-Cycloalkyl in the context of the invention represents cyclopropyl, cyclopentyl, cyclobutyl, cyclohexyl, cycloheptyl or cyclooctyl. Cyclopropyl, cyclopentyl and cyclohexyl may be mentioned as being preferred. The meaning of $(C_3–C_6)$-cycloalkyl is correspondingly advantageously cyclopropyl, cyclopentyl, cyclobutyl, cyclohexyl.

Halogen in the context of the invention generally represents fluorine, chlorine, bromine and iodine. Preference is given to fluorine, chlorine and bromine. Particular preference is given to fluorine and chlorine.

$(C_1–C_6)$-Alkanoyl in the context of the invention represents formyl and $(C_1–C_5)$-alkylcarbonyl groups, where $(C_1–C_5)$-alkyl may be a straight-chain or branched alkyl group having 1 to 5 carbon atoms, for example acetyl, propionyl, butyryl, pentanoyl.

A 5- or 6-membered aromatic heterocycle having up to 3 heteroatoms from the group consisting of S, O and N represents, for example, pyridyl, pyrimidyl, thienyl, furyl, pyrrolyl, thiazolyl, N-triazolyl, oxazolyl or imidazolyl. Preference is given to pyridyl, furyl, thiazolyl and N-triazolyl.

A 5- or 6-membered aromatic benzo-fused heterocycle having up to 3 heteroatoms from the group consisting of S, O and N represents, for example, benzimidazolyl.

A 5- or 6-membered saturated heterocycle attached via a nitrogen atom, which can be formed from two substituent groups together with the nitrogen atom to which they are attached, and which may optionally contain a further heteroatom from the group consisting of S and O or a radical of the formula $—NR^{15}$, in which $R^{15}$ is as defined above, generally represents, in the context of the invention, morpholinyl, piperidinyl, piperazinyl, methylpiperazinyl, thiomorpholinyl or pyrrolidinyl. Particular preference is given to morpholinyl, piperidinyl, pyrrolidinyl and thiomorpholinyl.

A 3- to 8-membered saturated or unsaturated nonaromatic heterocycle which is optionally attached via a nitrogen atom and which has up to 3 heteroatoms from the group consisting of S, N and O includes, for example, the abovementioned 5- or 6-membered saturated heterocycles which are attached via a nitrogen atom, and also 3-, 7- and 8-membered heterocycles, such as, for example, aziridines (for example 1-azacyclopropan-1-yl), azetidines (for example 1-azacyclobutan-1-yl) and azepines (for example 1-azepan-1-yl). The unsaturated representatives may contain 1 or 2 double bonds in the ring.

The side-group of a naturally occurring α-amino acid in the meaning of $R^{10}$ includes, for example: hydrogen (glycine), methyl (alanine), propan-2-yl (valine), 2-methylpropan-1-yl (leucine), 1-methyl-propan-1-yl (isoleucine), a propan-1,3-diyl group which is attached to the nitrogen atom of the amino group (proline), a 2-hydroxypropane-1,3-diyl group which is attached to the nitrogen atom of the amino group (hydroxyproline), a group of the formula

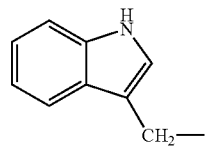

(tryptophan), a benzyl group (phenylalanine), a methylthioethyl group (methionine), hydroxymethyl (serine), p-hydroxybenzyl (tyrosine), 1-hydroxy-ethan-1-yl (threonine), mercaptomethyl (cysteine), carbamoylmethyl (asparagine), carbamoylethyl (glutamine), carboxymethyl (aspartic acid), carboxyethyl (glutamic acid), 4-aminobutan-1-yl (lysine), 3-guanidinopropan-1-yl (arginine), imidazol-4-ylmethyl (histidine), 3-ureidopropan-1-yl (citrulline), mercaptoethyl (homocysteine), hydroxyethyl (homoserine), 4-amino-3-hydroxybutan-1-yl (hydroxylysine), 3-aminopropan-1-yl (ornithine), etc.

In a further embodiment, the invention relates to compounds of the general formula (I) according to Claim 1:

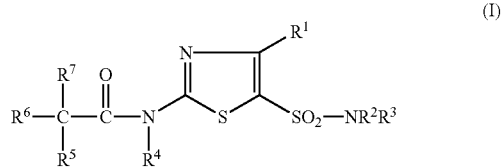

in which $R^1$ represents hydrogen, halogen, $(C_1–C_6)$-alkyl, $(C_1–C_6)$-alkoxy, amino-$(C_1–C_6)$-alkyl or halogeno-$(C_1–C_6)$-alkyl, $R^2$ and $R^3$ are identical or different and represent hydrogen, $(C_1–C_6)$-alkoxy, $(C_3–C_8)$-cycloalkyl or biphenylaminocarbonyl, or represent $(C_1–C_6)$-alkyl which is optionally substituted by 1 to 3 substituents selected from the group consisting of $(C_3–C_6)$-cycloalkyl, $(C_1–C_6)$-alkoxy, halogen, hydroxyl, amino, radicals of the formula

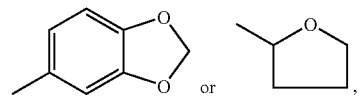

a 5- or 6-membered aromatic heterocycle having up to 3 heteroatoms from the group consisting of S, N and O, where a nitrogen-containing heterocycle may also be attached via the nitrogen atom, a 3- to 8-membered saturated or unsaturated nonaromatic heterocycle having up to 3 heteroatoms from the group consisting of S, N and O, which may optionally be attached via a nitrogen atom, and $(C_6–C_{10})$-aryl, which for its part may be substituted by hydroxyl or $(C_1–C_6)$-alkoxy, or represent a group of the formula

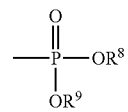

in which $R^8$ and $R^9$ are identical to or different from one another and represent hydrogen and $(C_1–C_4)$-alkyl, or represent a group of the formula

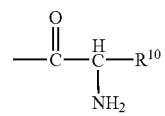

in which $R^{10}$ is the side-group of a naturally occurring α-amino acid, or represent a group of the formula

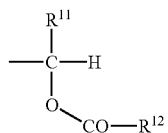

in which $R^{11}$ represents $(C_1-C_4)$-alkyl and $R^{12}$ represents hydrogen, $(C_1-C_4)$-alkyl or represents a group of the formula

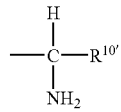

in which $R^{10'}$ is the side-group of a naturally occurring α-amino acid, or $R^2$ and $R^3$ together with the nitrogen atom form a 5- or 6-membered saturated heterocycle which may optionally contain an oxygen atom, $R^4$ represents hydrogen, $(C_1-C_6)$-acyl, $(C_2-C_6)$-alkenyl, $(C_3-C_8)$-cycloalkyl, or $R^4$ represents $(C_1-C_6)$-alkyl which may optionally be substituted by 1 to 3 substituents selected from the group consisting of halogen, hydroxyl, $(C_1-C_6)$-acyl, $(C_1-C_6)$-alkoxy, $-(OCH_2CH_2)_nOCH_2CH_3$, in which n is 0 or 1, phenoxy, $(C_6-C_{10})$-aryl and $-NR^{13}R^{14}$, in which $R^{13}$ and $R^{14}$ are identical or different and represent hydrogen, $(C_1-C_6)$-acyl, $(C_1-C_6)$-alkyl, carbamoyl, mono- or di-$(C_1-C_6)$-alkylamino-$(C_1-C_6)$-alkyl, mono- or di-$(C_1-C_6)$-alkylaminocarbonyl, $(C_6-C_{10})$-aryl or $(C_1-C_6)$-alkoxycarbonyl, or $R^{13}$ and $R^{14}$ together with the nitrogen atom form a 5- or 6-membered saturated heterocycle which may optionally contain a further heteroatom from the group consisting of S and O or a radical of the formula $-NR^{15}$ and which may be substituted by oxo, in which $R^{15}$ represents hydrogen or $(C_1-C_4)$-alkyl, or $R^4$ represents $(C_1-C_6)$-alkyl which is substituted by a 5- or 6-membered aromatic, optionally benzo-fused heterocycle having up to 3 heteroatoms from the group consisting of S, N and O, where a nitrogen-containing heterocycle may also be attached via the nitrogen atom, or which is substituted by radicals of the formulae

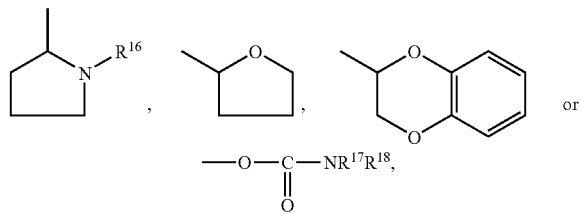

in which $R^{16}$ represents hydrogen or $(C_1-C_6)$-alkyl, $R^{17}$ and $R^{18}$ are identical or different and represent hydrogen, $(C_1-C_6)$-alkyl or $(C_6-C_{10})$-aryl, where abovementioned $(C_1-C_6)$-alkyl and $(C_6-C_{10})$-aryl may optionally be substituted by 1 to 3 substituents selected from the group consisting of hydroxyl, $(C_1-C_6)$-alkoxy and halogen, $R^5$ represents hydrogen, $(C_1-C_6)$-alkyl, halogen, amino, mono- or di-$(C_1-C_6)$-alkylamino or represents $(C_1-C_6)$-alkanoylamino, $R^6$ represents phenyl which may optionally be substituted by one to three substituents selected from the group consisting of halogen, $(C_6-C_{10})$-aryl which may optionally be substituted by 1 to 3 substituents selected from the group consisting of $(C_1-C_6)$-alkanoyl, $(C_1-C_6)$-alkoxy, $(C_1-C_6)$-alkyl, halogen, $(C_1-C_6)$-alkoxycarbonyl, nitro, halogeno-$(C_1-C_6)$-alkyl, halogeno-$(C_1-C_6)$-alkoxy, amino, $(C_1-C_6)$-alkylthio, hydroxyl, carboxyl, carbamoyl, mono- or di-$(C_1-C_6)$-alkylaminocarbonyl, mono- or di-$(C_1-C_6)$-alkanoylamino, $(C_1-C_6)$-alkoxycarbonylamino, $(C_1-C_6)$-alkylsulphoxy, $(C_1-C_6)$-alkylsulphonyl, tri-$(C_1-C_6)$-alkylsilyloxy, a 3- to 8-membered saturated or unsaturated nonaromatic mono- or bicyclic heterocycle having up to 3 heteroatoms from the group consisting of S, N and O, which may optionally be attached via a nitrogen atom, and/or cyano, $(C_1-C_6)$-alkoxy, $(C_1-C_6)$-alkoxycarbonyl, $(C_1-C_6)$-alkylthio, hydroxyl, carboxyl, partially fluorinated $(C_1-C_6)$-alkoxy having up to 6 fluorine atoms, $(C_1-C_6)$-alkyl which is optionally substituted by a radical of the formula

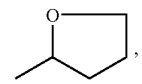

a 5- or 6-membered aromatic heterocycle having up to 3 heteroatoms from the group consisting of S, N and O which may optionally be attached via a nitrogen atom and which may optionally be substituted by 1 to 3 substituents selected from the group consisting of $(C_1-C_6)$-alkanoyl, $(C_1-C_6)$-alkoxy, $(C_1-C_6)$-alkyl, halogen, $(C_1-C_6)$-alkoxycarbonyl, nitro, halogeno-$(C_1-C_6)$-alkyl, halogeno-$(C_1-C_6)$-alkoxy, amino, $(C_1-C_6)$-alkylthio, hydroxyl, carboxyl, carbamoyl, mono- or di-$(C_1-C_6)$-alkylaminocarbonyl, mono- or di-$(C_1-C_6)$-alkanoylamino, $(C_1-C_6)$-alkoxycarbonylamino, $(C_1-C_6)$-alkylsulphoxy, $(C_1-C_6)$-alkylsuphonyl, a 3- to 8-membered saturated or unsaturated nonaromatic mono- or bicyclic heterocycle having up to 3 heteroatoms from the group consisting of S, N and O which may optionally be attached via a nitrogen atom, and/or cyano, a 3- to 8-membered saturated or unsaturated nonaromatic mono- or bicyclic heterocycle having up to 3 heteroatoms from the group consisting of S, N and O, which may optionally be attached via a nitrogen atom and which may optionally be substituted by 1 to 3 substituents selected from the group consisting of oxo, halogen, hydroxyl, $(C_1-C_6)$-alkoxycarbonyl, $(C_1-C_6)$-alkoxycarbonylamino, $(C_1-C_6)$-alkyl, halogeno-$(C_1-C_6)$-alkyl and hydroxy-$(C_1-C_6)$-alkyl, and groups of the formulae $-OR^{19}$, $-NR^{20}R^{21}$ or $-CO-NR^{22}R^{23}$, in which R$^{19}$ is phenyl which for its part is optionally substituted by a group of the formula —NR$^{24}$R$^{25}$ in which R$^{24}$ and R$^{25}$ are identical or different and represent hydrogen, (C$_1$–C$_6$)-alkyl or (C$_1$–C$_6$)-acyl, or R$^{19}$ represents (C$_1$–C$_6$)-alkyl which is optionally mono- to trisubstituted by hydroxyl and/or halogen, R$^{20}$ and R$^{21}$ are identical or different and represent hydrogen, carbamoyl, mono- or di-(C$_1$–C$_6$)-alkylaminocarbonyl, phenyl, (C$_1$–C$_6$)-acyl or (C$_1$–C$_6$)-alkyl, where abovementioned (C$_1$–C$_6$)-alkyl is optionally substituted by (C$_1$–C$_6$)-alkoxy, (C$_1$–C$_6$)-acyl, by phenyl or by a 5- or 6-membered aromatic heterocycle having up to 3 heteroatoms from the group consisting of S, N and O, where abovementioned phenyl and abovementioned aromatic heterocycle are optionally mono- to trisubstituted by identical or different substituents from the group consisting of halogen and hydroxyl, and R$^{22}$ and R$^{23}$ are identical or different and represent hydrogen or (C$_1$–C$_6$)-alkyl, and R$^7$ may have the meaning of R$^5$ and may be identical to or different from R$^5$, and their salts.

In a preferred embodiment, the invention relates to compounds of the general formula (I) in which R$^1$ represents hydrogen or (C$_1$–C$_6$)-alkyl.

In a further preferred embodiment, the invention relates to compounds of the general formula (I) in which R$^2$ and R$^3$ each independently represent hydrogen or (C$_1$–C$_6$)-alkyl.

In a further preferred embodiment, the invention relates to compounds of the general formula (I) in which R$^4$ represents hydrogen or (C$_1$–C$_6$)-alkyl.

In a further preferred embodiment, the invention relates to compounds of the general formula (I) in which R$^5$ represents hydrogen.

In a further preferred embodiment, the invention relates to compounds of the general formula (I) in which R$^6$ represents phenyl which may optionally be substituted by one to three substituents selected from the group consisting of halogen, (C$_6$–C$_{10}$)-aryl which may optionally be substituted by 1 to 3 substituents selected from the group consisting of (C$_1$–C$_6$)-alkanoyl, (C$_1$–C$_6$)-alkoxy, (C$_1$–C$_6$)-alkyl, halogen, (C$_1$–C$_6$)-alkoxycarbonyl, nitro, halogeno-(C$_1$–C$_6$)-alkyl, halogeno-(C$_1$–C$_6$)-alkoxy, amino, hydroxyl, mono- or di-(C$_1$–C$_6$)-alkylamino, mono- or di-(C$_1$–C$_6$)-alkanoylamino, (C$_1$–C$_6$)-alkoxycarbonylamino, and/or cyano, a 5- or 6-membered aromatic heterocycle having up to 3 heteroatoms from the group consisting of S, N and O, which may optionally be attached via a nitrogen atom and which may optionally be substituted by 1 or 2 halogen atoms.

In a further preferred embodiment, the invention relates to compounds having the following formula:

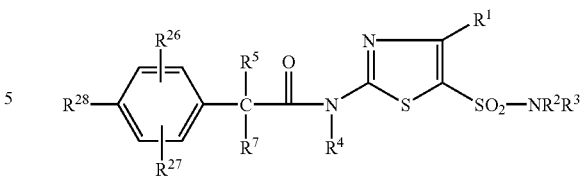

in which

R$^1$, R$^2$, R$^3$, R$^4$, R$^5$ and R$^7$ are each as defined in Claim 1,

R$^{26}$ and R$^{27}$ are identical or different and represent hydrogen, halogen, (C$_1$–C$_6$)-alkoxy, (C$_1$–C$_6$)-alkoxycarbonyl, (C$_1$–C$_6$)-alkylthio, hydroxyl, carboxyl, partially fluorinated (C$_1$–C$_6$)-alkoxy having up to 6 fluorine atoms, (C$_1$–C$_6$)-alkyl, a group of the formula —OR$^{19}$, —NR$^{20}$R$^{21}$ or —CO—NR$^{22}$R$^{23}$, in which R$^{19}$ represents phenyl which for its part is optionally substituted by a group of the formula —NR$^{24}$R$^{25}$, in which R$^{24}$ and R$^{25}$ are identical or different and represent hydrogen, (C$_1$–C$_6$)-alkyl or (C$_1$–C$_6$)-acyl, or R$^{19}$ represents (C$_1$–C$_6$)-alkyl which is optionally mono- to trisubstituted by hydroxyl and/or halogen, R$^{20}$ and R$^{21}$ are identical or different and represent hydrogen, carbamoyl, mono- or di-(C$_1$–C$_6$)-alkylaminocarbonyl, phenyl, (C$_1$–C$_6$)-acyl or (C$_1$–C$_6$)-alkyl, where abovementioned (C$_1$–C$_6$)-alkyl is optionally substituted by (C$_1$–C$_6$)-alkoxy, (C$_1$–C$_6$)-acyl, phenyl or by a 5- or 6-membered aromatic heterocycle having up to 3 heteroatoms from the group consisting of S, N and O, where abovementioned phenyl and abovementioned aromatic heterocycle are optionally mono- to trisubstituted by identical or different substituents from the group consisting of halogen and hydroxyl, and R$^{22}$ and R$^{23}$ are identical or different and represent hydrogen or (C$_1$–C$_6$)-alkyl, R$^{28}$ represents (C$_6$–C$_{10}$)-aryl, which may optionally be substituted by 1 to 3 substituents selected from the group consisting of (C$_1$–C$_6$)-alkanoyl, (C$_1$–C$_6$)-alkoxy, (C$_1$–C$_6$)-alkyl, halogen, (C$_1$–C$_6$)-alkoxycarbonyl, nitro, halogen-(C$_1$–C$_6$)-alkyl, halogen-(C$_1$–C$_6$)-alkoxy, amino, (C$_1$–C$_6$)-alkylthio, hydroxyl, carboxyl, carbamoyl, mono- or di-(C$_1$–C$_6$)-alkylaminocarbonyl, mono- or di-(C$_1$–C$_6$)-alkanoylamino, (C$_1$–C$_6$)-alkoxycarbonylamino, (C$_1$–C$_6$)-alkylsulphoxy, (C$_1$–C$_6$)-alkylsulphonyl, tri-(C$_1$–C$_6$)-alkylsilyloxy, a 3- to 8-membered saturated or unsaturated nonaromatic mono- or bicyclic heterocycle having up to 3 heteroatoms from the group consisting of S, N and O, which may optionally be attached via a nitrogen atom, and/or cyano, or R$^{28}$ represents a 5- or 6-membered aromatic heterocycle having up to 3 heteroatoms from the group consisting of S, N and O, which may optionally be attached via a nitrogen atom and which may optionally be substituted by 1 to 3 substituents selected from the group consisting of (C$_1$–C$_6$)-alkanoyl, (C$_1$–C$_6$)-alkoxy, (C$_1$–C$_6$)-alkyl, halogen, (C$_1$–C$_6$)-alkoxycarbonyl, nitro, halogeno-(C$_1$–C$_6$)-alkyl, halogeno-(C$_1$–C$_6$)-alkoxy, amino, (C$_1$–C$_6$)-alkylthio, hydroxyl, carboxyl, carbamoyl, monoor di-($C_1$–$C_6$)-alkylaminocarbonyl, mono- or di-($C_1$–$C_6$)-alkanoylamino, ($C_1$–$C_6$)-alkoxycarbonylamino, ($C_1$–$C_6$)-alkylsulphoxy, ($C_1$–$C_6$)-alkylsulphonyl, a 3- to 8-membered saturated or unsaturated nonaromatic mono- or bicyclic heterocycle having up to 3 heteroatoms from the group consisting of S, N and O, which may optionally be attached via a nitrogen atom, and/or cyano, and their salts.

Particular preference is, for example, given to the compound N-[5-(aminosulphonyl)-4-methyl-1,3-thiazol-2-yl]-2-[1,1'-biphenyl]4-yl-N-methylacetamide of the formula:

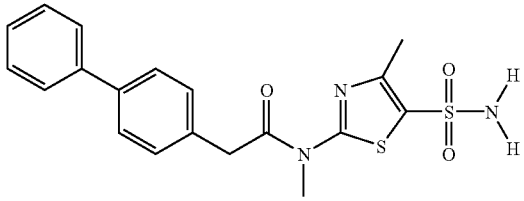

to the compound N-[5-(aminosulphonyl)-4-methyl-1,3-thiazol-2-yl]-2-(2'-fluoro[1,1'-biphenyl]-4-yl)-N-methylacetamide of the formula:

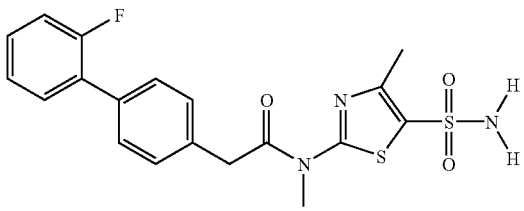

and to the compound N-[5-(aminosulphonyl)-4-methyl-1,3-thiazol-2-yl]-N-methyl-2-[4-(2-pyridinyl)phenyl]acetamide of the formula:

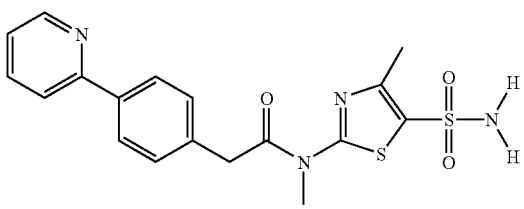

and to pharmaceutically acceptable salts thereof.

The invention furthermore relates to compounds of the general formula (IV)

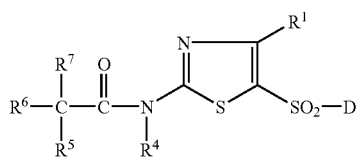

in which $R^1$, $R^4$, $R^5$, $R^6$ and $R^7$ each have the meaning given for the formula (I) and D represents a halogen atom.

The invention furthermore relates to processes for preparing the compounds of the general formula (I), characterized in that

[A] compounds of the general formula (II)

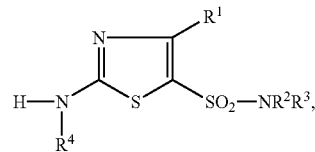

in which $R^1$, $R^2$, $R^3$ and $R^4$ are each as defined above, are reacted with compounds of the general formula (III)

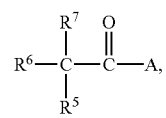

in which

A represents a leaving group, such as, for example, halogen, preferably chlorine, or hydroxyl, and $R^5$, $R^6$ and $R^7$ are each as defined above, in inert solvents, if appropriate in the presence of a base and/or an auxiliary, to give compounds of the formula (I),

[B] compounds of the general formula (IV)

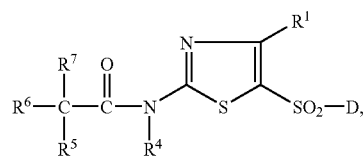

in which $R^1$, $R^4$, $R^5$, $R^6$ and $R^7$ are each as defined above and D represents a halogen atom, preferably chlorine, are reacted with amines of the general formula (V)

$HNR^2R^3$  (V), in which $R^2$ and $R^3$ are each as defined above, in inert solvents, to give compounds of the formula (I),

[C] compounds of the general formula (X)

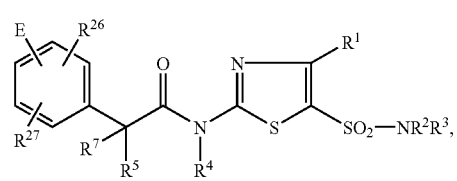

in which $R^1$, $R^2$, $R^3$, $R^4$, $R^5$, $R^7$, $R^{26}$ and $R^{27}$ are each as defined above and E represents trifluoromethanesulphonate or halogen, preferably bromine or iodine, are reacted with boronic acids or stannanes of the general formula (XI)

$$R^{28}M \quad (XI),$$

in which

R$^{28}$ is as defined above and M may be, for example, a tri-(C$_1$–C$_6$)-alkylstannyl group, such as a trimethylstannyl group, or a boronic acid group, in inert solvents in the presence of palladium catalysts, for example tetrakis(triphenylphosphane) palladium(0), if appropriate in the presence of a base, for example potassium phosphate, at temperatures of 50–140° C., to give compounds of the formula (XIV)

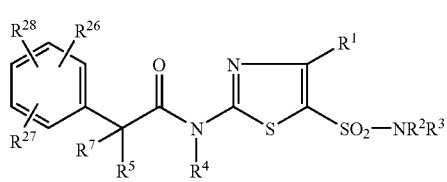
(XIV)

and

[D] compounds of the general formula (XII)

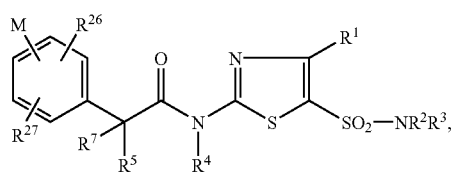
(XII)

in which

R$^1$, R$^2$, R$^3$, R$^4$, R$^5$, R$^7$, R$^{26}$ and R$^{27}$ are each as defined above and M is as defined above, are reacted with trifluoromethanesulphonates or halides of the general formula (XIII):

$$R^{28}E \quad (XIII),$$

in which

R$^{28}$ is as defined above and E is as defined above, in inert solvents in the presence of palladium catalysts, for example tetrakis(triphenylphosphane)palladium (0), if appropriate in the presence of a base, for example potassium phosphate, at temperatures of 50–140° C., to give compounds of the formula (XIV).

The process [A] according to the invention can be illustrated in an exemplary manner by the following equation:

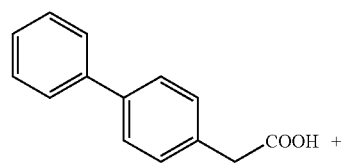
COOH +

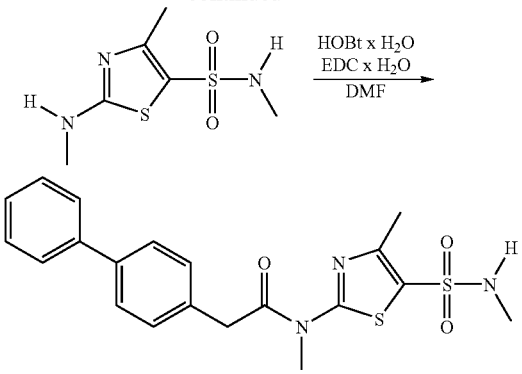

The abbreviations denote:

HOBt: 1-hydroxy-1H-benzotriazole
EDC: N'-(3-dimethylaminopropyl)-N-ethylcarbodiimide× HCl
DMF: N,N-dimethylformamide The process [C] according to the invention can be illustrated in an exemplary manner by the following equation:

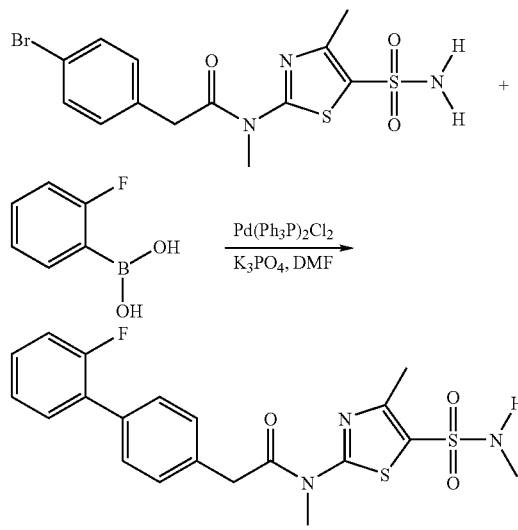

The abbreviation denotes:

DMF: N,N-dimethylformamide

The process [D] according to the invention can be illustrated in an exemplary manner by the following equation:

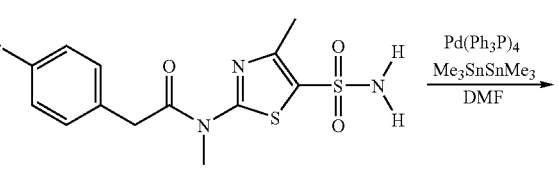

-continued

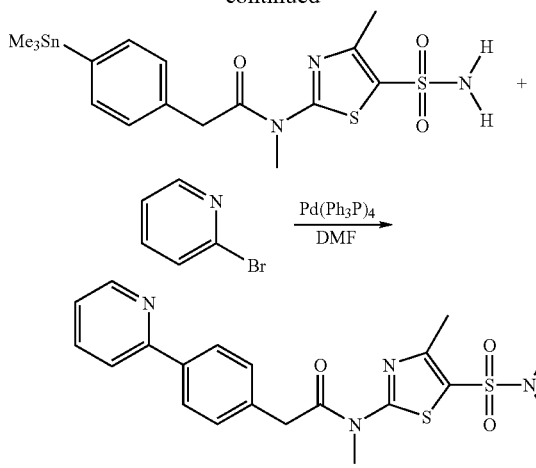

The abbreviation denotes:

DMF: N,N-dimethylformamide

Suitable solvents for the processes [A], [B], [C] and [D] are the customary organic solvents which do not change under the reaction conditions. These preferably include ethers, such as diethyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethylene, trichloroethylene or chlorobenzene, or ethyl acetate, dimethyl sulphoxide, dimethylformamide (DMF) or acetonitrile. It is also possible to use mixtures of the solvents mentioned. Preference is given to DMF.

Suitable bases for use in the process [A] according to the invention are, in general, inorganic or organic bases. These preferably include organic amines (trialkyl($C_1$–$C_6$)amines), such as triethylamine, or heterocycles, such as 1,4-diazabicyclo[2.2.2]octane (DABCO), 1,8-diazabicyclo[5.4.0]undec-7-ene (DBU), pyridine, diaminopyridine, N-methylmorpholine or N-methylpiperidine or morpholine. Preference is given to triethylamine.

Suitable auxiliaries are dehydrating or coupling reagents which are known per se, such as, for example, carbodiimides, such as diisopropylcarbodiimide, dicyclohexylcarbodiimide (DCC) or N-(3-dimethylaminopropyl)-N'-ethylcarbodiimide (EDC), or carbonyl compounds, such as carbonyldiimidazole (CDI) or isobutyl chloroformate, or 1,2-oxazolium compounds, such as 2-ethyl-5-phenyl-1,2-oxazolium-3'-sulphonate, or phosphorus compounds, such as propanephosphonic anhydride, diphenylphosphoryl azide, benzotriazolyl-N-oxy-tris(dimethylamino)phosphonium hexafluorophosphate (BOP), or uronium compounds, such as O-benzotriazol-1-yl-N,N,N',N'-tetramethyluronium hexafluorophosphate (HBTU), or methanesulphonyl chloride, if appropriate in the presence of auxiliaries, such as N-hydroxysuccinimide or N-hydroxybenzotriazole.

In general, the base is employed in an amount of from 0.05 mol to 10 mol, preferably from 1 mol to 2 mol, based on 1 mol of the compound of the formula (III).

The processes according to the invention are generally carried out in a temperature range of from −50° C. to +100° C., preferably from −30° C. to +60° C.

The processes according to the invention are generally carried out at atmospheric pressure. However, it is also possible to carry out the processes at elevated pressure or at reduced pressure (for example in a range of from 0.5 to 5 bar).

The compounds of the general formula (II) can be prepared, for example, by converting compounds of the general formula (VI)

in which $R^1$ is as defined above by reaction with the system chlorosulphonic acid/$SOCl_2$ into the compounds of the general formula (VII)

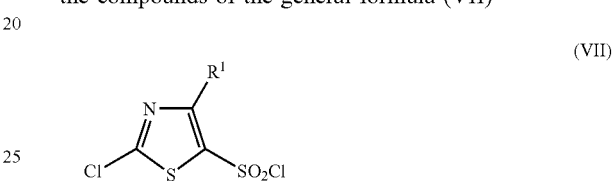

in which $R^1$ is as defined above, then, using amines of the general formula (V)

$HNR^2R^3$ (V)

in which $R^2$ and $R^3$ are each as defined above in inert solvents, preparing the compounds of the general formula (VIII)

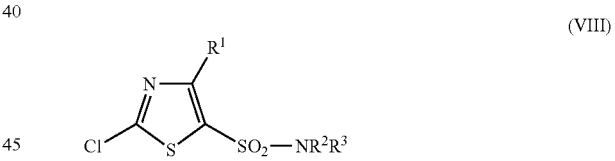

in which $R^1$, $R^2$ and $R^3$ are each as defined above and, in a last step, carrying out a reaction with amines of the general formula (IX)

$H_2N—R^{4'}$ (IX)

in which $R^{4'}$ has the meaning of $R^4$ given above and is identical to or different from $R^4$, but is not hydrogen, in inert solvents and in the presence of a base.

The reaction with chlorosulphonic acid/$SO_2Cl$ is initially carried out at room temperature and then at the reflux temperature of the ether in question.

The reaction is generally carried out under atmospheric pressure. However, it is also possible to carry out the process at elevated pressure or at reduced pressure (for example in a range of from 0.5 to 5 bar).

Suitable solvents for the reaction with the amines of the general formula (V) are alcohols, such as, for example, methanol, ethanol, propanol and isopropanol. Preference is given to methanol.

The reaction with the amines of the general formula (V) is initially carried out at room temperature and then at the reflux temperature of the ether in question.

The reaction is generally carried out at atmospheric pressure. However, it is also possible to carry out the process at elevated pressure or at reduced pressure (for example in a range of from 0.5 to 5 bar).

The reaction with the compounds of the general formula (IX) is carried out in ethers, such as, for example, Methyl ether, dioxane, tetrahydrofuran or glycol dimethyl ether. Preference is given to methanol.

Suitable for use as bases are, in general, inorganic or organic bases. These preferably include organic amines (tri($C_1$–$C_6$)alkylamines, such as triethylamine), or heterocycles, such as 1,4-diazabicyclo[2.2.2]octane (DABCO), 1,8-diazabicyclo-[5.4.0]undec-7-ene (DBU), pyridine, diaminopyridine, methylpiperidine or morpholine. Preference is given to triethylamine.

In general, the base is employed in an amount of from 0.05 to 10 mol, preferably from 1 mol to 2 mol, based on 1 mol of the compound of the formula (VIII).

Some of the compounds of the general formula (VI) are known, or they can be prepared by customary methods [cf. Hantzsch, Chem. Ber. 1927, 60, 2544].

The compounds of the general formulae (VII) and (VIII) are novel and can be prepared as described above.

Amines of the general formulae (V) and (IX) are known.

Compounds of the general formula (III) are known or can be prepared by processes known from the literature.

Biphenylmethylcarboxylic acid or biphenylacetic acid derivatives of the formula (III) can be prepared in a manner known per se by transition-metal-catalysed, for example palladium-catalysed, coupling reactions, such as, for example, the Suzuki or Stille coupling. The pyridylphenyl-methylcarboxylic acid derivatives of the formula (III) are known from the literature (see, for example, M. Artico et al. in *Eur. J. Med. Chem.* (1992) 27, 219–228), or they can be prepared by processes known per se. The reaction schemes A, B, C and D below illustrate, in an exemplary manner, the synthesis of biphenylacetic acid derivatives from the corresponding boronic acids and the synthesis of pyridylphenylacetic acid derivatives from the corresponding stannyl compounds:

A:

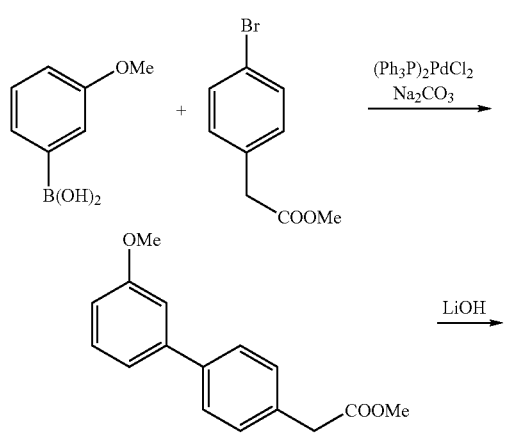

B:

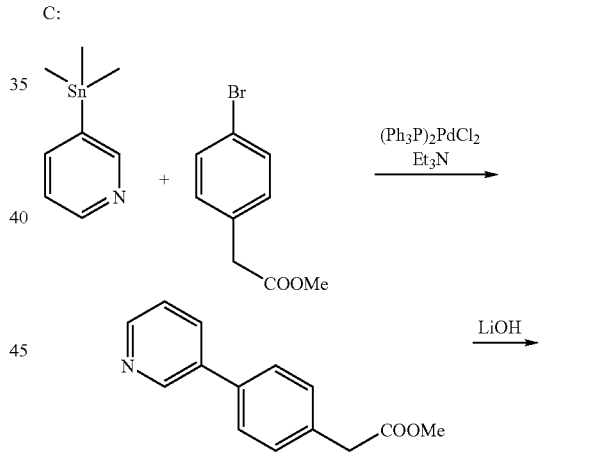

C:

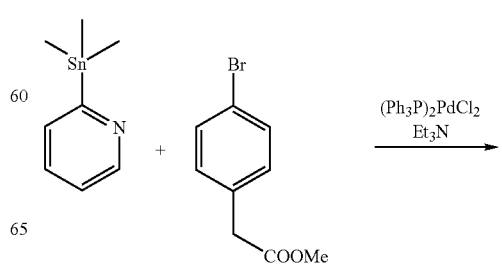

D:

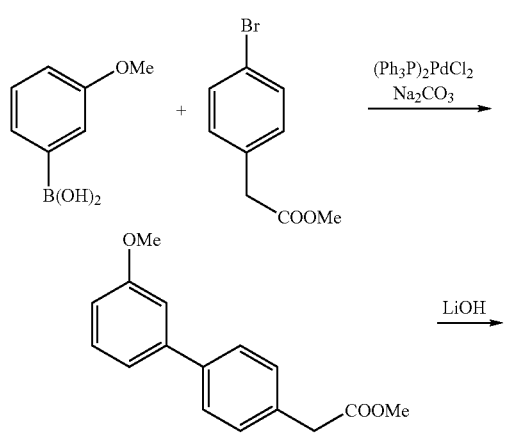

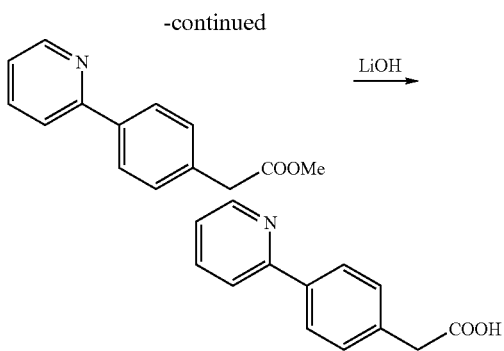

Compounds of the formula (III) in which $R^5$ and $R^7$ are fluorine, for example, can be prepared by the process shown in the reaction scheme below:

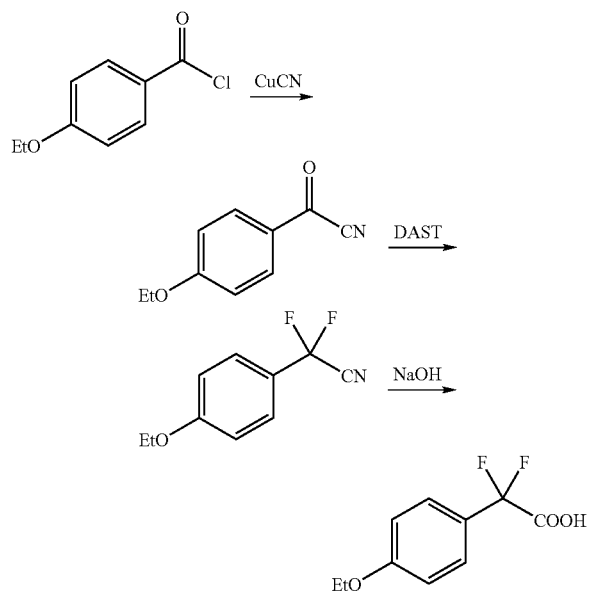

The fluorination with DAST (N,N-diethylaminosulphur trifluoride) is carried out in accordance with J. Fluor. Chem. 61, 1993, 117.

The invention furthermore relates to the use of the compounds of the formula (I) as medicaments.

The invention furthermore relates to a pharmaceutical composition which comprises a compound of the general formula (I) in a mixture with at least one pharmaceutically acceptable carrier or excipient.

The invention furthermore relates to the use of a compound of the general formula (I) for preparing a medicament, in particular a medicament for the treatment and/or prevention of viral infections, such as herpes viruses, in particular Herpes simplex viruses.

The invention furthermore relates to the use of N-[5-(aminosulphonyl)-1,3-thiazol-2-yl]acetamide derivatives, preferably N-[5-(aminosulphonyl)-1,3-thiazol-2-yl]-2-phenylacetamide derivatives, more preferably N-[5-(aminosulphonyl)-1,3-thiazol-2-yl]-2-[1,1'-biphenyl]-4-ylacetamide derivatives, for preparing medicaments, in particular to the use of the derivatives mentioned for preparing compositions for the treatment and/or prevention of viral infections in humans or animals, such as infections caused by herpes viruses, in particular by Herpes simplex viruses. Here, N-[5-(aminosulphonyl)-1,3-thiazol-2-yl] acetamide derivatives, N-[5-(aminosulphonyl)-1,3-thiazol-2-yl]-2-phenylacetamide derivatives and N-[5-(aminosulphonyl)-1,3-thiazol-2-yl]-2-[1,1'-biphenyl]-4-ylacetamide derivatives are to be understood as meaning those compounds which are derived from N-[5-(aminosulphonyl)-1,3-thiazol-2-yl]acetamide, N-[5-(aminosulphonyl)-1,3-thiazol-2-yl]-2-phenylacetamide and N-[5-(aminosulphonyl)-1,3-thiazol-2-yl]-2-[1,1'-biphenyl]-4-ylacetamide by the substitution of one or more hydrogen atoms.

The compounds of the general formula (I) according to the invention exhibit an unforeseeable surprising spectrum of action. They exhibit an antiviral action against representatives of the Herpes viridae group, particularly against Herpes simplex viruses (HSV). They are thus suitable for the treatment and prophylaxis of disorders which are caused by herpes viruses, in particular disorders which are caused by Herpes simplex viruses.

In Vitro Activity

Viruses and Cells:

HSV (HSV-1 Walki, HSV-1F or HSV-2G) was cultivated on Vero cells (ATCC CCL-81) under the following conditions: The cells were grown in M199 medium (5% foetal calf serum, 2 mM glutamine, 100 IU/ml penicillin, 100 µg/ml streptomycin) in cell culture bottles at 37° C. and 5% $CO_2$. The cells were splitted twice per week, in each case 1:4. For the infection, the medium was removed, the cells were washed with Hank's solution, detached using 0.05% trypsin, 0.02% EDTA (Seromed L2143) and incubated at a density of $4 \times 10^5$ cells per ml under the abovementioned conditions for 24 hours. The medium was then removed and the virus solution was added at an m.o.i of <0.05 in a volume of 2 ml per 175 $cm^2$ of surface. The medium was incubated under the conditions mentioned for one hour and then made up to a volume of 50 ml per 175 $cm^2$ bottle. 3 days after the infection, the cultures showed clear signs of a cytopathic effect. The virus was released by freezing (−80° C.) and thawing (37° C.) the cultures twice. Cell debris was removed by centrifugation (300 g, 10 min, 4° C.) and the supernatant was frozen down in aliquots at −80° C.

The virus titre was determined using a plaque assay. To this end, Vero cells were seeded in 24-well plates at a density of $4 \times 10^5$ cells per well and, after 24 hours of incubation (37° C., 5% $CO_2$) infected with dilutions of the virus stock of from $10^{-2}$ to $10^{-12}$ (100 µl of inoculum). 1 hour after the infection, the medium was removed and the cells were covered with 1 ml of overlay medium (0.5% methylcellulose, 0.22% sodium bicarbonate, 2 mM glutamine, 100 IU/ml penicillin, 100 µg/ml streptomycin, 5% foetal calf serum in MEM-Eagle medium with Earl's salt) and incubated for 3 days. The cells were then fixated using 4% formaline for 1 hour, washed with water, stained with Giemsa (Merck) for 30 min and then washed and dried. Using a plaque viewer, the virus titre was determined. The virus stocks used for the experiments had a titre of $1 \times 10^6$/ml–$1 \times 10^8$/ml.

The anti-HSV action was determined in a screening test system in 96-well microtitre plates using various cell lines of neuronal, lymphoid and epithelial origin, such as, for example, Vero (kidney cell line of the green monkey), MEF (murine embryonal fibroblasts), HELF (humane embryonal fibroblasts), NT2 (humane neuronal cell line) or Jurkat (humane lymphoid T-cell line). The effect of the substances on the spreading of the cytopathogenic effect was determined in comparison to the reference substance acyclovir-sodium (Zovirax$^R$), a clinically approved anti-herpes chemotherapeutic.

The substances (50 mM), dissolved in DMSO (dimethyl sulphoxide), are examined on microtitre plates (for example 96-well MTP) in final concentrations of 250–0.5 µM (micromolar) in two replications (4 substances/plate). In the case of potent substances, the dilutions are continued for several plates up to 0.5 pM (picomolar). Also examined are toxic and cytostatic effects of the substances. After an appropriate dilution of the substances (1:2) on the microtitre plate in medium, a suspension of cells ($1 \times 10^4$ cells per well) such as, for example, of Vero cells in M199 (medium 199) with 5% foetal calf serum, 2 mM glutamine and optionally 100 IU/ml penicillin and 100 µg/ml streptomycin or of MEF cells in EMEM (Eagle's Minimum Essential Medium) with 10% foetal calf serum, 2 mM glutamine and optionally 100 IU/ml penicillin and 100 µg/ml streptomycin, or of HELF cells in EMEM with 10% foetal calf serum, 2 mM glutamine and optionally 100 IU/ml penicillin and 100 µg/ml streptomycin, or of NT2- and Jurkat cells in DMEM (4.5 mg/l glucose plus pyridoxin) with 10% foetal calf serum, 2 mM glutamine, 1 mM sodium pyruvate, non-essential amino acids and optionally 100 IU/ml penicillin and 100 µg/ml streptomycin is added to each well and the cells in the relevant wells are infected with an appropriate amount of virus (HSV-1 F or HSV-2 G having an m.o.i (multiplicity of infection) of 0.0025 for HELF, Vero and MEF cells and an m.o.i of 0.1 for NT2 and Jurkat cells). The plates are then incubated at 37° C. in a $CO_2$ incubator (5% $CO_2$) for several days. After this time, the cell lawn of, for example, Vero cells in the substance-free virus controls, starting from 25 infection centres, is completely destroyed or lysed by the cytopathogenic effect of the HSV viruses (100% CPE). The plates are initially evaluated visually using a microscope and then analysed using a fluorescent dye. To this end, the cell supernatant of all wells of the MTP is aspirated and the wells are filled with 200 µl of PBS wash solution. The PBS is then aspirated and all the wells are filled with 200 µl of fluorescent dye solution (fluorescein diacetate, 10 µg/ml in PBS). After an incubation time of 30–90 min, the test plates are read in a fluorescence detector at an excitation wavelength of 485 nm and an emission wavelength of 538 nm.

The results for some compounds are summarized in the table below.

TABLE

| Example | IC50 HSV-1 F/Vero | IC50 HSV-2 G/Vero |
|---|---|---|
| 14 | 0.1 µM | 0.75 µM |
| 57 | <0.01 µM | <0.01 µM |
| 8 | 0.1 µM | 0.1 µM |
| 23 | 0.03 µM | 0.1 µM |
| 38 | 0.05 µM | 0.016 µM |
| 87 | <0.01 µM | <0.01 µM |
| 126 | 0.01 µM | 0.1 µM |
| Zovirax (aciclovir-sodium) | 1 µM | 3 µM |

Here, $IC_{50}$ is the half-maximal fluorescence intensity with respect to the non-infected cell control (100% value). The $IC_{50}$ value can also be referenced to a suitable active compound control (see description of the assay: infected cells in the presence of suitable concentrations of a substance having anti-herpes action, such as, for example, Zovirax 20 µM). This active compound control reaches fluorescence intensities of about 85 to 95% with respect to the cell control.

Preference is given to N-[5-(aminosulphonyl)-1,3-thiazol-2-yl]acetamide derivatives according to the invention whose $IC_{50}$ (HSV-1 F/Vero) in the in-vitro screening test system described above is preferably below 50 µM, more preferably below 25 µM and very particularly preferably below 10 µM.

The compounds according to the invention are thus useful active compounds for the treatment and prophylaxis of disorders caused by herpes viruses, in particular Herpes simplex viruses. Examples of indication areas which may be mentioned are:

1) Treatment and prophylaxis of herpes infections, in particular Herpes simplex infections in patients displaying symptoms such as Herpes labialis, Herpes genitalis, and HSV-related keratitis, encephalitis, pneumonia, hepatitis etc.
2) Treatment and prophylaxis of herpes infections, in particular Herpes simplex infections, in patients with a suppressed immune system (for example AIDS patients, cancer patients, patients having a genetic immunodeficiency, transplant patients)
3) Treatment and prophylaxis of herpes infections, in particular Herpes simplex infections, in new-born children and infants
4) Treatment and prophylaxis of herpes infections, in particular Herpes simplex infections, and in herpes-positive patients, in particular Herpes-simplex-positive patients, for suppressing recurrence (suppression therapy)

In-Vivo Action

Animals:

6 week-old female mice, BALB/cABom strain were obtained from a commercial breeder (Bomholtgard Breeding and Research Centre Ltd.).

Infection:

The animals were anaesthetized with diethyl ether (Merck) in a sealed glass vessel. 50 µl of a dilution of the virus stock (infection dose $5 \times 10^4$ Pfu) were introduced into the nose of the anaesthetized animals using an Eppendorf pipette. In 90–100% of the animals, this infection dose causes death by a generalized infection with prominent respiratory and central-nervous symptoms on average after 5 to 8 days.

Treatment and Assessment:

6 hours after the infection, the animals were treated with doses of 0.1–100 mg/kg of body mass, 3 times per day, at 7 a.m., 2 p.m. and 7 p.m., for a period of 5 days. The substances were pre-dissolved in DMSO and resuspended in tylose/PBS (Hoechst) (final concentration 1.5% DMSO, 0.5% tylose in PBS).

After the last administration, the animals were monitored further and the time of death was determined.

A comparison of the survival curves showed for the compound of Example 57, for example, an $ED_{50}$ of about 0.7 mg/kg for HSV-2, where $ED_{50}$ means that 50% of the animals survive at this dose.

The novel active compounds can be converted in a known manner into the customary formulations, such as tablets, sugar-coated tablets, pills, granules, aerosols, syrups, emulsions, suspensions and solutions, using inert, nontoxic, pharmaceutically suitable carriers and solvents. Here, the therapeutically active compound should in each case be present in a concentration of about 0.5 to 90% by weight of the total mixture, i.e. in amounts which are sufficient to achieve the dosage range indicated.

The formulations are prepared, for example, by extending the active compounds with solvents and/or excipients, if appropriate using emulsifiers and/or dispersants, it being possible, for example, if the diluent used is water, to use, if appropriate, organic solvents as auxiliary solvents.

Administration is carried out in a customary manner, preferably orally, parenterally or topically, in particular perlingually or intravenously.

In the case of parenteral administration, solutions of the active compounds using suitable liquid carrier materials can be employed.

In general, it has proved advantageous in the case of intravenous administration to administer amounts of from approximately 0.001 to 20 mg/kg, preferably approximately 0.01 to 10 mg/kg, of bodyweight to achieve effective results, and in the case of oral administration the dose is approximately 0.01 to 30 mg/kg, preferably 0.1 to 20 mg/kg, of bodyweight.

In spite of this, it may be necessary, if appropriate, to depart from the amounts mentioned, namely depending on the bodyweight or on the type of administration route, on the individual response to the medicament, the manner of its formulation and the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide this into several individual administrations over the course of the day.

If appropriate, it may be useful to combine the compounds according to the invention with other active substances, in particular antiviral active substances.

Starting Materials

EXAMPLE I

2-Chloro-4-methyl-1,3-thiazol-5-sulphonyl chloride

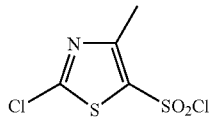

At room temperature, 150 g (1.12 mol) of 2-chloro-4-methyl-1,3-thiazole are added dropwise to a solution of 331 g (2.81 mol) of thionyl chloride in 653 g (5.61 mol) of chlorosulphonic acid. The solution is heated at reflux for 48 h. The mixture is then poured into 3 l of ice-water and extracted with 4×400 ml of dichloromethane. The combined organic phases are washed with 2.5 l of water, dried over sodium sulphate and concentrated. Distillation of the crude product gives 233.7 g of product in the form of an oil. (Bp 87–96° C., 0.7 mbar, GC 98.1%, yield 89.6%).

EXAMPLE II

2-Chloro-4-methyl-1,3-thiazol-5-sulphonamide

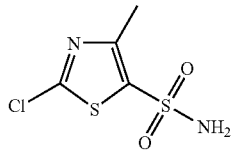

At −10° C., 117.7 g (1.8 mol) of a 26% strength aqueous ammonia solution are added dropwise to a solution of 208 g (95% strength, 0.9 mol) of 2-chloro-4-methyl-1,3-thiazole-5-sulphonyl chloride in 1000 ml of tetrahydrofuran. The mixture is stirred without further cooling for 2 h and the reaction mixture is then concentrated using a rotary evaporator. The crude product is used for the next step without further purification.

EXAMPLE III

4-Methyl-2-(methylamino)-1,3-thiazole-5-sulphonamide

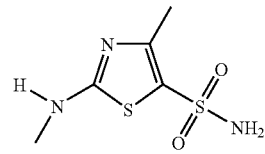

At room temperature, 144 g (0.576 mol) of 2-chloro-4-methyl-1,3-thiazole-5-sulphonamide are initially charged in 600 ml of acetonitrile, and 147 g (1.9 mol) of a 40% strength aqueous methylamine solution are metered in at room temperature. The reaction mixture is stirred at 50° C. for 6 h and then concentrated using a rotary evaporator. The residue is admixed with water, filtered off with suction and dried.

Yield: 78 g (66%) M.p.: 194° C.

EXAMPLE IV

2-Fluorophenylboronic acid

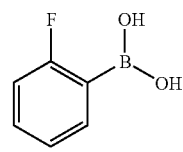

Under argon, 155 g (0.86 mol) of 2-fluorobromobenzene are initially charged in 732 ml of absolute tetrahydrofuran and, at −78° C., mixed slowly with 600 ml of 1.6 M n-butyllithium in hexane. The mixture is then stirred at −78° C. for 2 h. At −78° C., 298 ml (1.28 mol) of trimethyl borate are then added dropwise. After 1 h, cooling is removed, and the reaction mixture is stirred overnight and warmed to room temperature. For work-up, the mixture is, at 0° C., mixed with 346 ml of saturated ammonium chloride solution, the pH is adjusted to pH 6 using 1N HCl and the aqueous phase is extracted 3 times with in each case 250 ml of methylene chloride. The combined organic phases are washed with saturated sodium chloride solution and dried with magnesium sulphate. This gives Example IV in the form of a beige solid.

Yield: 60.0 g (48%) MS (EI, m/z): 140 (80%, [M]$^+$), 96 (100%, [C$_6$H$_5$F]$^+$)

EXAMPLE V

Methyl (2'-fluoro[1,1'-biphenyl]-4-yl)acetate

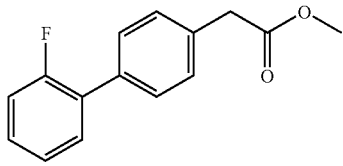

Under argon, 47.6 g (0.21 mol) of methyl 4-bromophenylacetate are initially charged in 400 ml of absolute tetrahydrofuran and, at room temperature, admixed with 320 ml of 1M sodium carbonate solution and 40 g of (0.28 mol) of 2-fluorophenylboronic acid. 7.0 g (0.01 mol) of bis(triphenylphosphane)palladium(II) chloride are added, and the mixture is then heated under reflux for 18 h. After cooling, the mixture is diluted with 500 ml of water and extracted three times with in each case 300 ml of ethyl acetate. The combined organic phases are washed with in each case 400 ml of saturated ammonium chloride solution, water and saturated sodium chloride solution, dried over magnesium sulphate and freed from the solvent under reduced pressure. Example V is obtained after silica gel filtration (petroleum ether/ethyl acetate 10:1) as a colourless oil.

Yield: 46.0 g (94%) $^1$H-NMR (500 MHz, CDCl$_3$, δ/ppm): 3.71 (s, 2H), 3.76 (s, 3H), 7.18–7.46 (m, 4H) 7.40 (d, J=8.3 Hz; 2H), 7.56 (dd, J$_1$=8.3 Hz, J$_2$=1.7 Hz; 2H).

EXAMPLE VI (2'-Fluoro[1,1'-biphenyl]4-yl)acetic acid

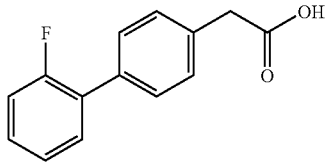

26.5 g (0.11 mol) of methyl (2'-fluoro[1,1'-biphenyl]-4-yl)acetate are initially charged in 50 ml of ethanol and, at room temperature, admixed with a solution of 12.8 g (0.19 mol) of potassium hydroxide pellets in 25 ml of water. The mixture is then heated under reflux for 4 h. After cooling, the crude mixture is concentrated under reduced pressure, and the residue is dissolved in 100 ml of water and acidified using conc. hydrochloric acid. The precipitate is filtered off and washed repeatedly with water, and the solid is dried. This gives Example VI in the form of white crystals.

Yield: 22.7 g (91%) M.p.: 102° C. $^1$H-NMR (500 MHz, CDCl$_3$, δ/ppm): 3.74 (s, 2H), 7.18–7.47 (m, 4H), 7.41 (d, J=8.2 Hz; 2H), 7.57 (dd, J$_1$=8.2 Hz, J$_2$=1.6 Hz; 2H).

EXAMPLE VII

Methyl [4-(2-pyridinyl)phenyl]acetate

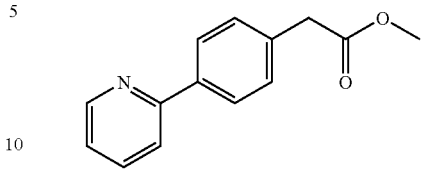

Under argon, 7.85 g (34.3 mmol) of methyl 4-bromophenylacetate are initially charged in 95 ml of toluene and, at room temperature, admixed with 7.97 g (61.7 mmol) of diisopropylethylamine, 9.50 g (37.7 mmol) of 2-trimethyl-stannylpyridine and 0.4 g (0.3 mmol) of tetrakis(triphenylphosphane)palladium(0). The mixture is then heated under reflux for 18 h. After cooling, the mixture is washed with in each case 100 ml of 1N hydrochloric acid and saturated sodium bicarbonate solution. The organic phase is discarded. The acidic and the basic aqueous phase are neutralized and in each case extracted with 100 ml of dichloromethane, and the combined organic phases are dried over sodium sulphate and freed from the solvent under reduced pressure. Example VII is obtained after silica gel chromatography (toluene/ethyl acetate gradient 5:1–1:1) as a colourless oil.

Yield: 1.6 g (19%) $^1$H-NMR (400 MHz, d$^6$-DMSO, δ/ppm): 3.64 (s, 3H), 3.76 (s, 2H), 7.33–7.40 (m, 1H), 7.39 (d, J=8.2 Hz; 2H), 7.86–7.90 (m, 1H), 7.96 (d, J=8.0 Hz; 1H), 8.05 (d, J=8.2 Hz; 2H), 8.67 (d, J=4.2 Hz, broad; 1H).

EXAMPLE VIII

[4-(2-Pyridinyl)phenyl]acetic acid

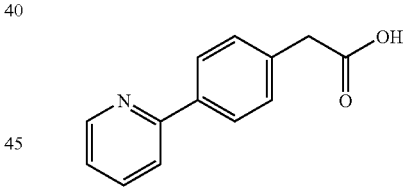

700 mg (3.11 mol) of methyl [4-(2-pyridinyl)phenyl]acetate are initially charged in 5 ml of tetrahydrofuran and, at room temperature, admixed with 6.2 ml of a 1M potassium hydroxide solution in water. The mixture is then stirred at room temperature for 18 h, most of the solvent is removed under reduced pressure and the residue is taken up in 10 ml of water and adjusted to a pH of about 5 using 2N hydrochloric acid. The aqueous phase was extracted twice, in each case with 10 ml of dichloromethane, the combined organic phases were dried over magnesium sulphate and the solvent was removed under reduced pressure, giving the compound of Example VIII in the form of a solid.

Yield: 300 mg (46%) $^1$H-NMR (400 MHz, d$^6$-DMSO, δ/ppm): 3.76 (s, 2H), 7.45–7.51 (m, 1H), 7.50 (d, J=8.3 Hz; 2H), 8.00 (td, J$_1$=7.7 Hz, J$_2$=1.9 Hz; 1H), 8.07 (d, J=7.9 Hz; 1 H), 8.15 (d, J=8.3 Hz; 2H), 8.78 (dt, J$_1$=4.0 Hz, J$_2$=0.9 Hz; 1H).

PREPARATION EXAMPLES

EXAMPLE 15

N-[5-(Aminosulphonyl)-4-methyl-1,3-thiazol-2-yl]-2-[1,1'-biphenyl]-4-yl-N-methylacetamide

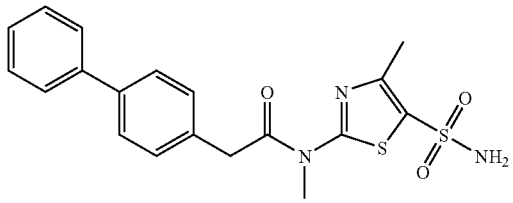

138.2 mg (0.65 mmol) of 4-biphenylacetic acid and 99.7 mg (0.65 mmol) of 1-hydroxy-1H-benzotriazole hydrate are initially charged at room temperature in 5 ml of dimethylformamide. 150 mg (0.72 mmol) of 2-methylamino-4-methyl-1,3-thiazole-5-sulphonamide and 138.7 mg (0.72 mmol) of N'-(3-dimethylaminopropyl)-N-ethylcarbodiimide hydrochloride are added, and the mixture is stirred at room temperature for 72 h. The reaction mixture is then filtered off with suction and the residue is recrystallized from 2-propanol. This gives a white solid.

Yield: 240 mg (83.0%) M.p.: 191° C. $^1$H-NMR (300 MHz, d$^6$-DMSO, δ/ppm): 2.47 (s, 3H; partially under the DMSO signal), 3.71 (s, 3H), 4.20 (s, 2H), 7.32–7.70 (m, 11H).

EXAMPLE 38

N-[5-(Aminosulphonyl)-4-methyl-1,3-thiazol-2-yl]-N-methyl-2-[4-(2-pyridinyl)phenyl]acetamide

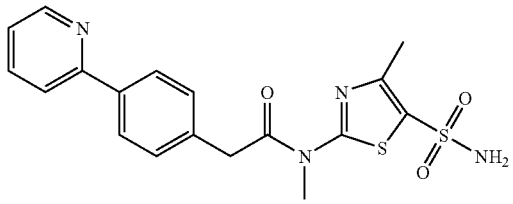

At room temperature, 300 mg (1.41 mmol) of [4-(2-pyridinyl)phenyl]acetic acid and 190 mg (1.41 mmol) of 1-hydroxy-1H-benzotriazole hydrate are initially charged in 4 ml of dimethylformamide. 307 mg (1.48 mmol) of 2-methylaminomethyl-1,3-thiazole-5-sulphonamide and 284 mg (1.48 mmol) of N'-(3-dimethylaminopropyl)-N-ethylcarbodiimide hydrochloride are added, and the mixture is stirred at room temperature for 18 h. The solvent is then removed under reduced pressure, the residue is taken up in toluene and the solvent is once more removed under reduced pressure. The residue is stirred with 15 ml of water and 3 ml of methanol and then filtered off, and the filtrate is re-extracted with 20 ml of dichloromethane. Solid and dichloromethane phase are combined and the solvent is removed under reduced pressure. This gives the compound of Example 38 in the form of a white solid.

Yield: 440 mg (74.0%) M.p.: 188–192° C. MS (ESI, m/z): 403 (100%, [M+H]$^+$) $^1$H-NMR (400 MHz, d$^6$-DMSO, δ/ppm): 2.38 (s, 3H; under the DMSO signal), 3.64 (s, 3H), 4.15 (s, 2H), 7.28–7.26 (m, 1H), 7.32 (d, J=8 Hz; 2H), 7.58 (s, 2H), 7.82–7.96 (m, 2H), 7.98 (d, J=8.0 Hz; 2H), 8.61 (m; 1H).

EXAMPLE 57

N-[5-(Aminosulphonyl)-4-methyl-1,3-thiazol-2-yl]-2-(2'-fluoro[1,1'-biphenyl]-4-yl)-N-methylacetamide

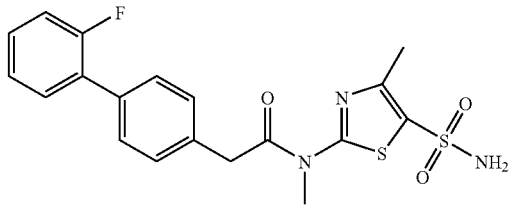

At room temperature, 17.33 g (73.3 mmol) of (2'-fluoro[1,1'-biphenyl]4-yl)acetic acid and 9.9 g (73.3 mmol) of 1-hydroxy-1H-benzotriazole hydrate are initially charged in 600 ml of dimethylformamide. 16.84 g (81.4 mmol) of 2-methylamino-4-methyl-1,3-thiazole-5-sulphonamide and 15.58 g (81.4 mmol) of N'-(3-dimethylaminopropyl)-N-ethylcarbodiimide hydrochloride are added, and the mixture is stirred at room temperature for 18 h. Most of the dimethylformamide is removed at 50° C. under high vacuum, and the residue is taken up in 400 ml of dichloromethane and then washed with in each case 350 ml of water and 10% citric acid solution. Drying over magnesium sulphate and removal of the solvent under reduced pressure gives the compound of Example 57 in the form of a white solid.

Yield: 23.2 g (76.0%) M.p.: 211° C. $^1$H-NMR (400 MHz, CDCl$_3$, δ/ppm): 2.58 (s, 3H), 3.73 (s, 3H), 4.07 (s, 2H), 5.91 (s, 2H), 7.13–7.46 (m, 4H), 7.34 (d, J=8.1 Hz; 2H), 7.56 (d, broad, J=8.1 Hz; 2H).

EXAMPLE 87

N-[5-(aminosulphonyl)-4-methyl-1,3-thiazol-2-yl]-2-(2',5'-difluoro-1,1'-biphenyl-4-yl)-N-methylacetamide

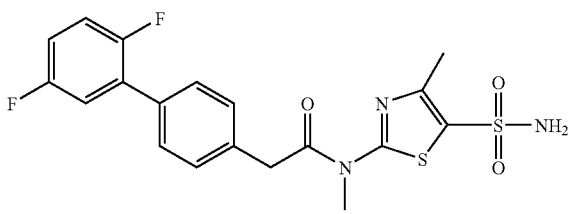

At room temperature, 1.00 g (4.0 mmol) of (2',5'-difluoro[1,1'-biphenyl]-4-yl)acetic acid and 0.54 g (4.0 mmol) of 1-hydroxy-1H-benzotriazole hydrate are initially charged in 15 ml of dimethylformamide. 0.84 g (4.0 mmol) of 2-methylamino-4-methyl-1,3-thiazole-5-sulphonamide and 0.77 g (4.0 mmol) of N'-(3-dimethylaminopropyl)-N-ethylcarbodiimide hydrochloride are added, and the mixture is stirred at room temperature for 18 h. Most of the dimethylformamide is removed at 50° C. under high vacuum, and the residue is stirred 3 times with in each case 50 ml of water and filtered off, stirred with 50 ml of isopropanol and filtered off once more. Removal of the solvent under reduced pressure gives the compound of Example 87 in the form of a slightly yellow solid.

Yield: 0.83 g (47.3%) M.p.: 184° C. $^1$H-NMR (400 MHz, DMSO, δ/ppm): 2.49 (s, 3H), 3.71 (s, 3H), 4.24 (s, 2H), 7.22–7.46 (m, 3H), 7.38 (d, J=8.2 Hz; 2H), 7.56 (d, J=8.2 Hz; 2H), 7.65 (s, 2H).

EXAMPLE 126

N-[5-(Aminosulphonyl)-4-methyl-1,3-thiazol-2-yl]-N-methyl-2-[4-(1H-pyrazol-1-yl)phenyl]acetamide

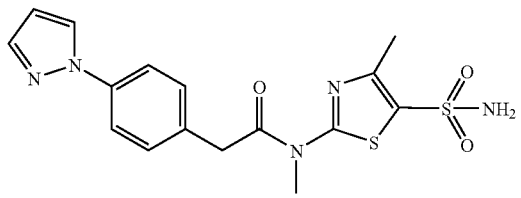

0.100 g (0.48 mmol) of 2-methylamino-4-methyl-1,3-thiazole-5-sulphonamide is dissolved in 10 ml of N,N-dimethylformamide and, at room temperature, admixed with 0.110 g (0.53 mmol) of [4-(1H-pyrazol-1-yl)phenyl]acetic acid, 0.070 g (0.53 mmol) of 1-hydroxy-1H-benzotriazole and 0.070 g (0.53 mmol) of N,N'-diisopropylcarbodiimide. The solution is stirred at room temperature overnight. The mixture is then poured into water and the aqueous phase is extracted 3 times with ethyl acetate. The combined organic phases are dried with sodium sulphate and concentrated. The crude product is subjected to fine purification on a preparative HPLC (RP18 column; mobile phase: acetonitrile/water gradient).

Yield: 0.11 g (59%) LC-MS (Method: SMKL-N1-1Low Vol HCl): retention time: 3.65 MS(ESI): 783 (2Mz+H), 392 (Mz+H). $^1$H-NMR (300 MHz, DMSO, δ/ppm): 2.48 (s, 3H), 3.72 (s, 3H), 4.20 (s, 2H), 6.55 (t, J=2 Hz; 1H), 7.38 (d, J=7 Hz; 2H), 7.65 (s, 2H), 7.75 (d, J=2 Hz; 1H), 7.82 (d, J=7 Hz; 2H), 8.49 (d, J=2 Hz; 1H).

The compounds listed in the table below are prepared analogously to the procedures given above:

| Ex. No. | Structure | M.p. [°C.] | Rf value | Rt [min] method |
|---|---|---|---|---|
| 1 | 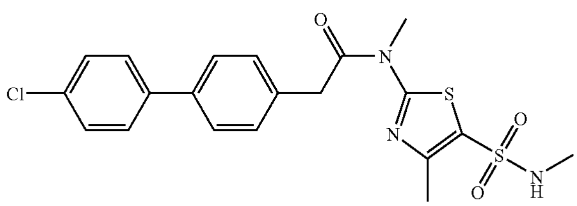 | 186 | | |
| 2 | 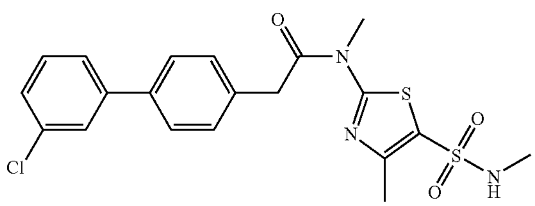 | 187 | | |
| 3 | 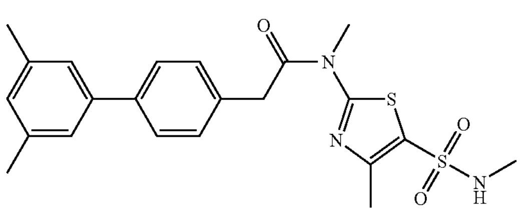 | 170 | | |
| 4 | 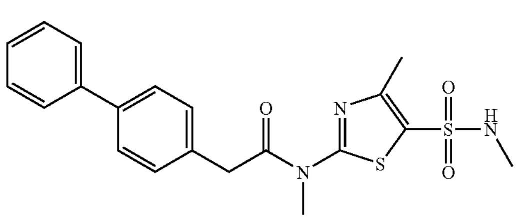 | 180 | | |

-continued

| Ex. No. | Structure | M.p. [° C.] | Rf value | Rt [min] method |
|---|---|---|---|---|
| 5 | (structure) | 154 | | |
| 6 | (structure) | 167 | | |
| 7 | (structure) | 192 | | |
| 8 | (structure) | 186 | | |
| 9 | (structure) | 109 | | |
| 10 | (structure) | 128 | | |

-continued

| Ex. No. | Structure | M.p. [° C.] | Rf value | Rt [min] method |
|---|---|---|---|---|
| 11 | 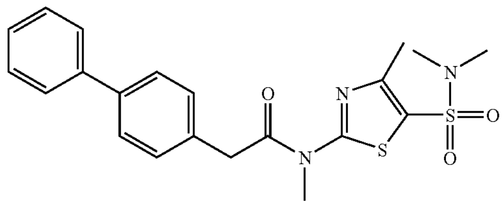 | 184 | | |
| 12 | 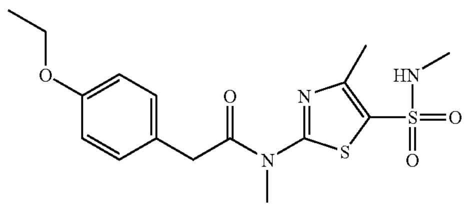 | 157 | | |
| 13 | 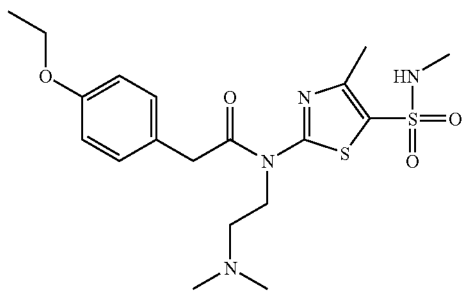 | 153 | | |
| 14 | 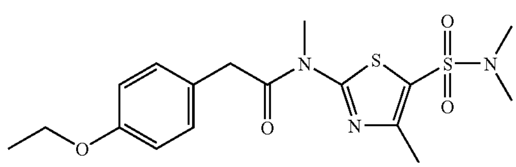 | 154 | | |
| 15 | 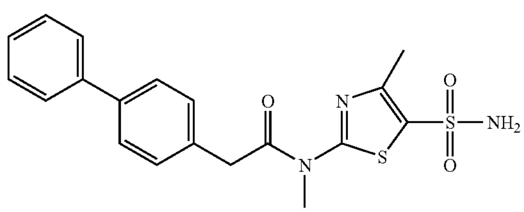 | 191 | | |
| 16 | 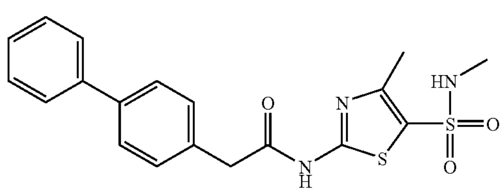 | 133 | | |
| 17 | 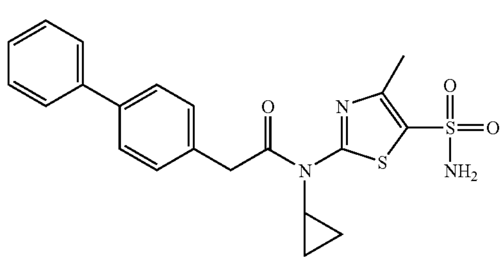 | 179 | | |

-continued

| Ex. No. | Structure | M.p. [° C.] | Rf value | Rt [min] method |
|---|---|---|---|---|
| 18 | 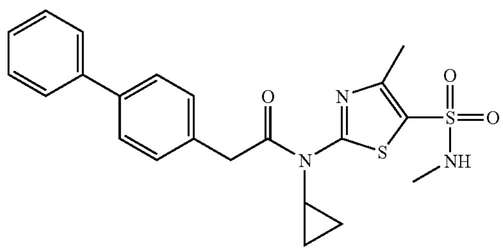 | 202 | | |
| 19 | 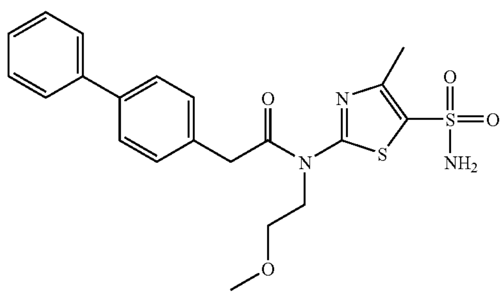 | 163 | | |
| 20 | 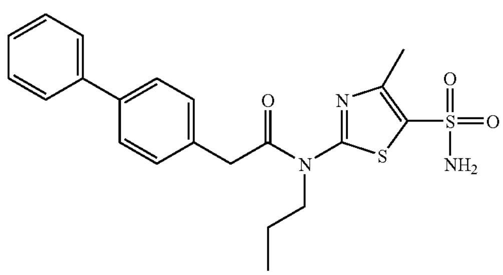 | 154 | | |
| 21 | 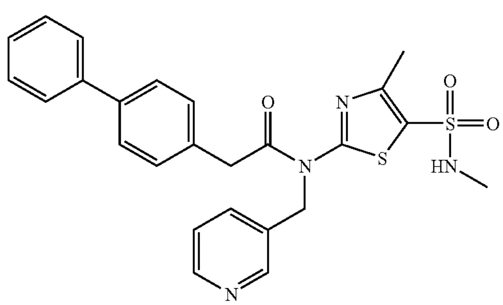 | 161 | | |
| 22 | 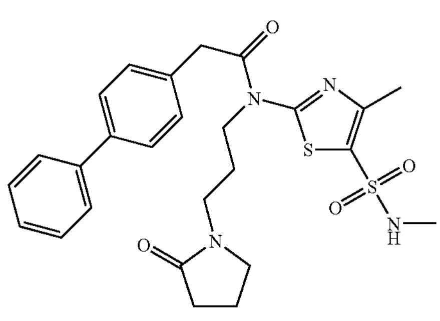 | 158 | | |

-continued

| Ex. No. | Structure | M.p. [° C.] | Rf value | Rt [min] method |
|---|---|---|---|---|
| 23 | 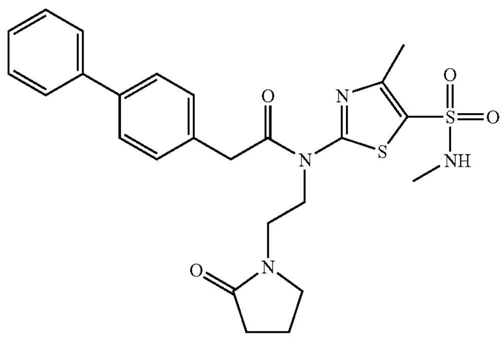 | 156 | | |
| 24 | 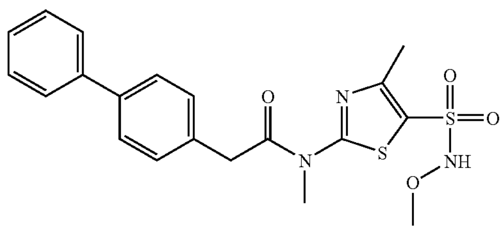 | 129 | | |
| 25 | 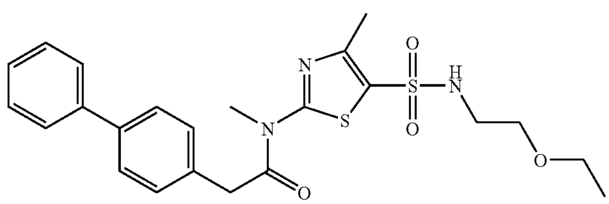 | 105–106 | | |
| 26 | 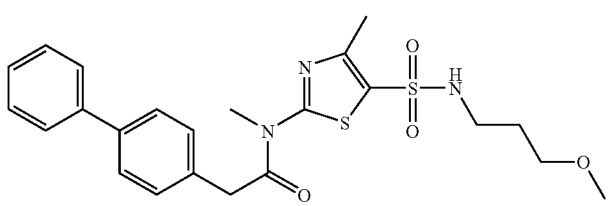 | 142–143 | | |
| 27 | 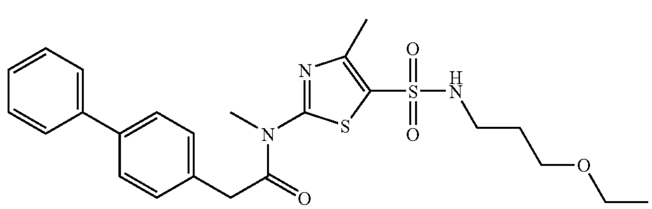 | 139–140 | | |
| 28 | 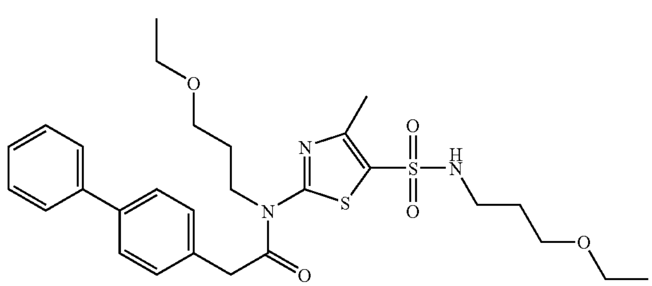 | oil | | 5.66 |

-continued

| Ex. No. | Structure | M.p. [° C.] | Rf value | Rt [min] method |
|---|---|---|---|---|
| 29 | 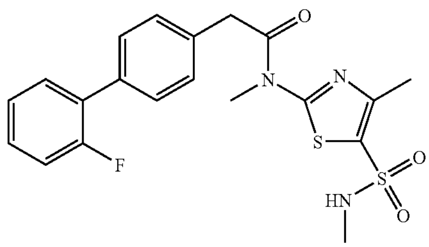 | 179 | | |
| 30 | 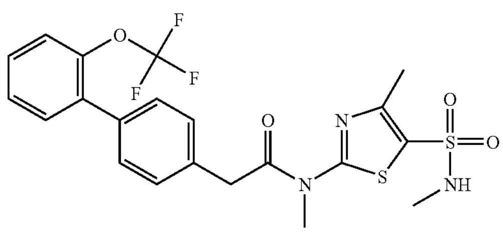 | 190 | | |
| 31 | 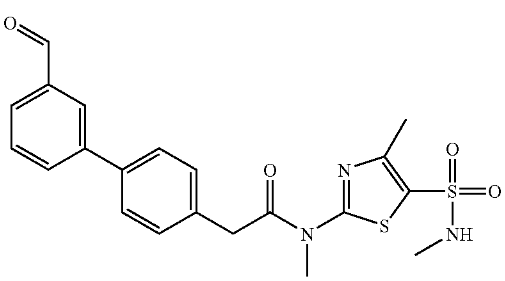 | 192 | | |
| 32 | 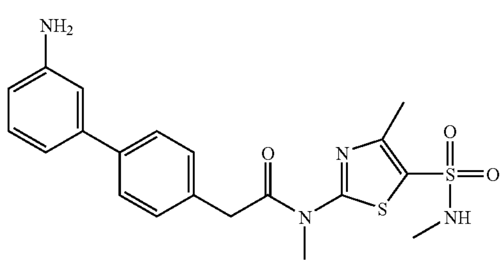 | 193 | | |
| 33 | 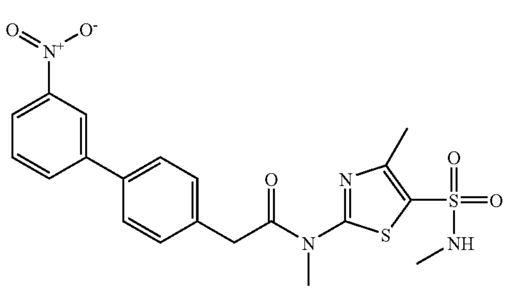 | 201 | | |

-continued

| Ex. No. | Structure | M.p. [° C.] | Rf value | Rt [min] method |
|---|---|---|---|---|
| 34 | 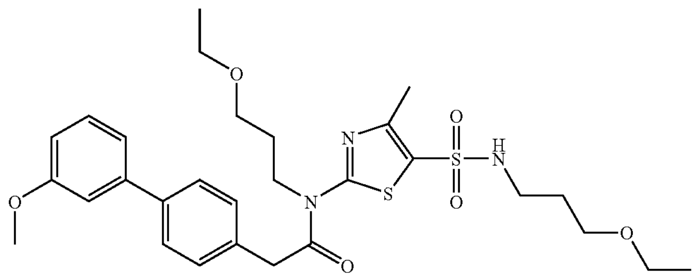 | 74–75 | | |
| 35 | 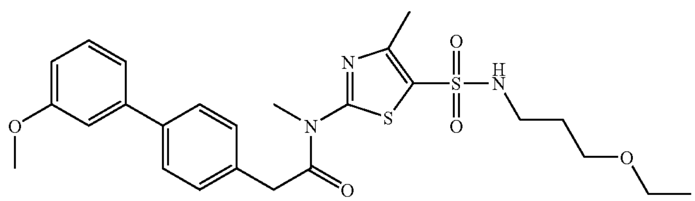 | 125–127 | | |
| 36 | 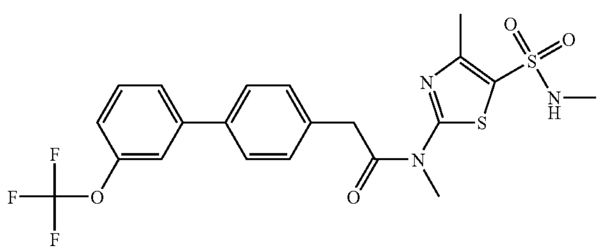 | 156 | | |
| 37 | 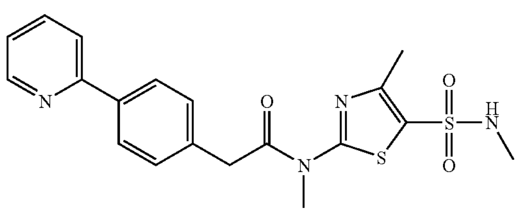 | oil | 0.11 CH2Cl2/ MeOH) 96:4) | |
| 38 | 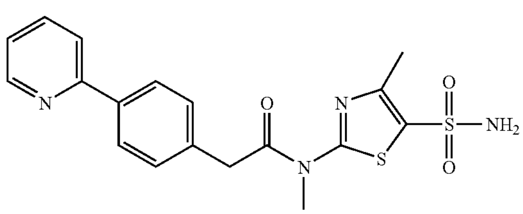 | 188–192 | | |
| 39 | 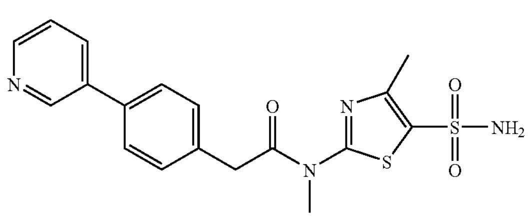 | 208 | | |

-continued

| Ex. No. | Structure | M.p. [° C.] | Rf value | Rt [min] method |
|---|---|---|---|---|
| 40 | 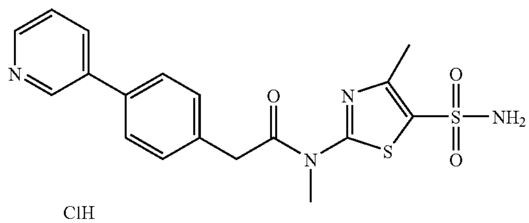 | 177 | | |
| 41 | 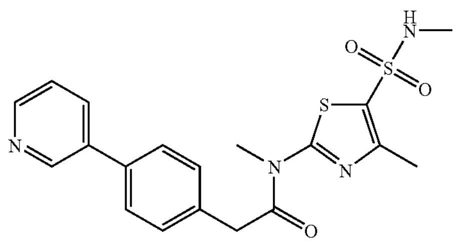 | 200 | | |
| 42 | 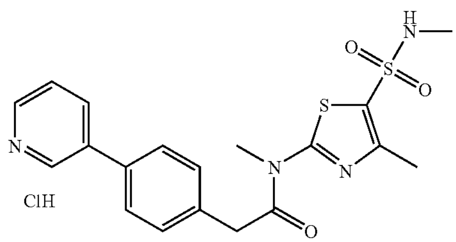 | 270 | | |
| 43 | 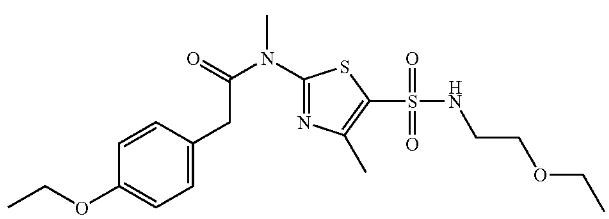 | 125–127 | | |
| 44 | 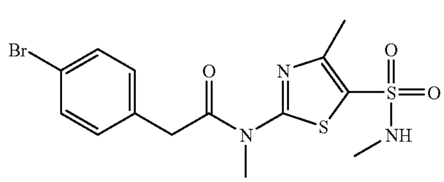 | 168 | | |
| 45 | 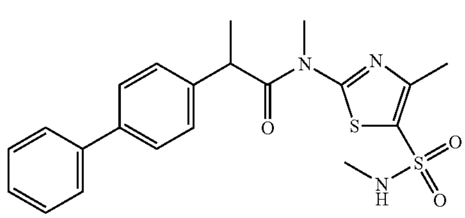 | 170–172 | | |

-continued

| Ex. No. | Structure | M.p. [° C.] | Rf value | Rt [min] method |
|---|---|---|---|---|
| 46 | 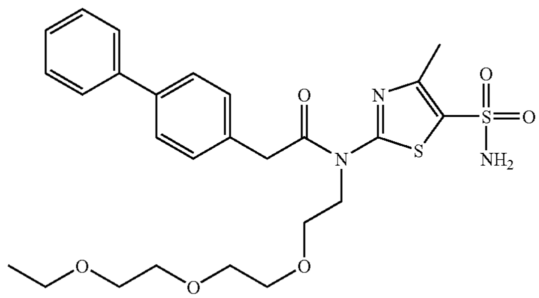 | 94 | | |
| 47 | 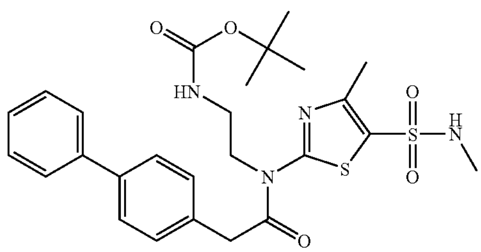 | 188 | | |
| 48 | 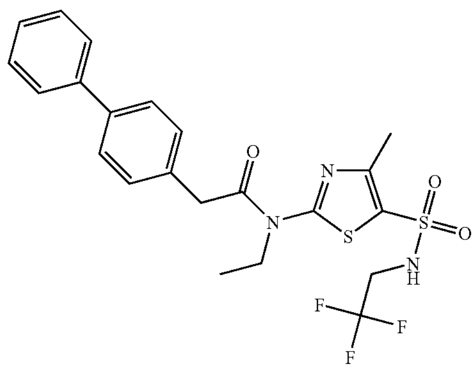 | 152 | | |
| 49 | 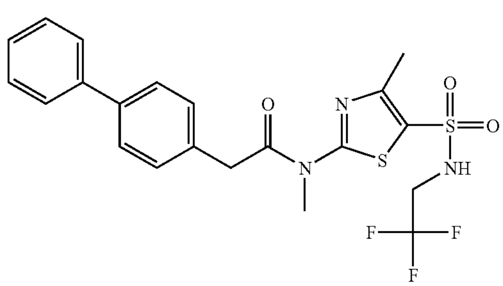 | 216 | | |
| 50 | 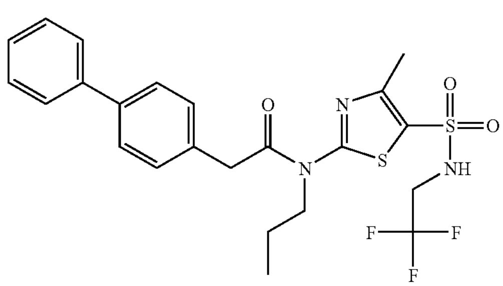 | 108 | | |

-continued

| Ex. No. | Structure | M.p. [° C.] | Rf value | Rt [min] method |
|---|---|---|---|---|
| 51 | 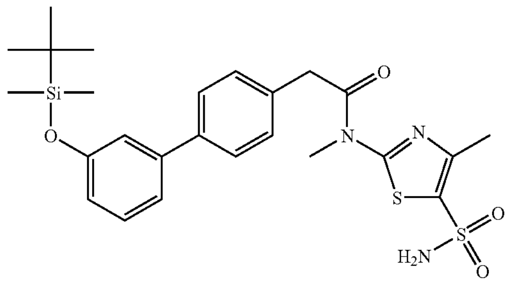 | 161 | | |
| 52 | 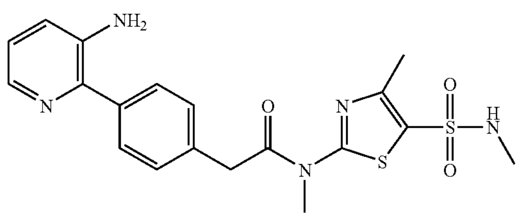 | 80 | | |
| 53 | 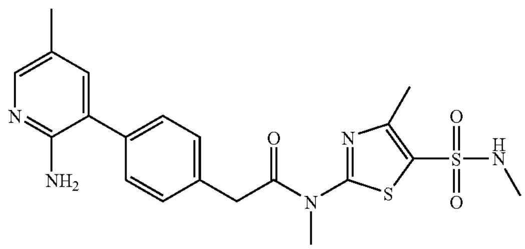 | | 0.30 (CH2Cl2/ MeOH 100:5) | |
| 54 | 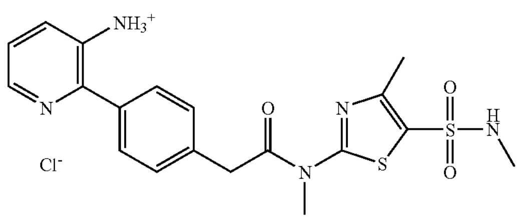 | 160 | | |
| 55 | 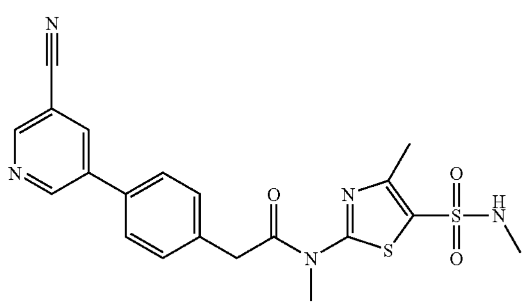 | 130 | | |
| 56 | 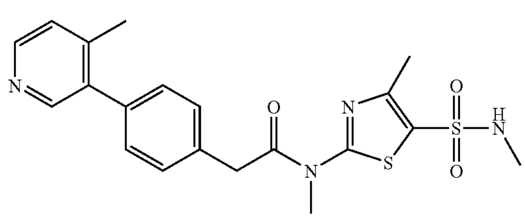 | 113 | | |

-continued

| Ex. No. | Structure | M.p. [° C.] | Rf value | Rt [min] method |
|---|---|---|---|---|
| 57 | 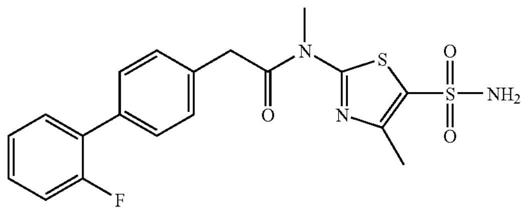 | 211 | | |
| 58 | 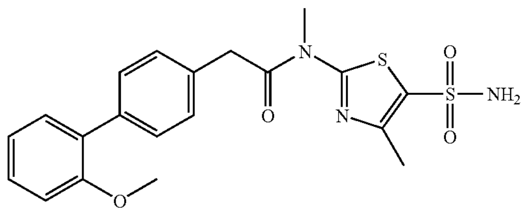 | 230 | | |
| 59 | 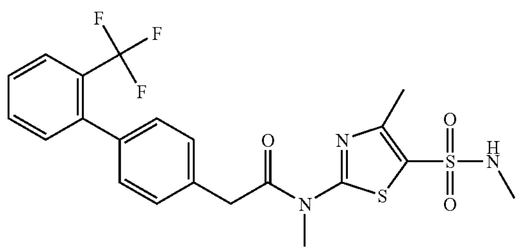 | 202 | | |
| 60 | 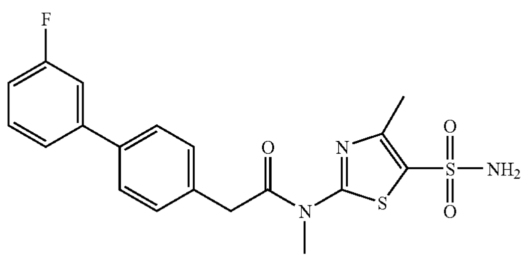 | 145 | | |
| 61 | 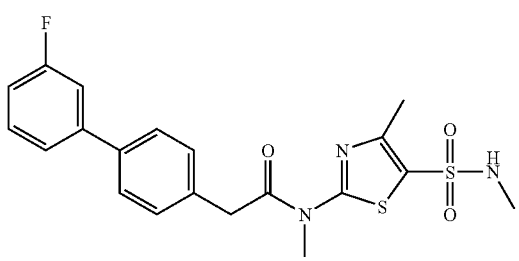 | 190 | | |
| 62 | 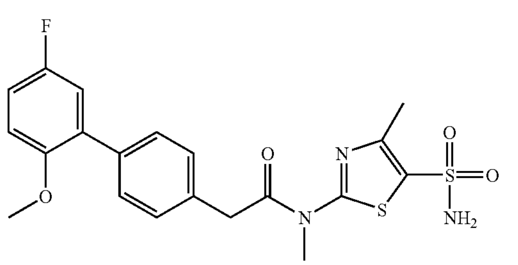 | 219 | | |

-continued
| Ex. No. | Structure | M.p. [° C.] | Rf value | Rt [min] method |
|---|---|---|---|---|
| 63 | 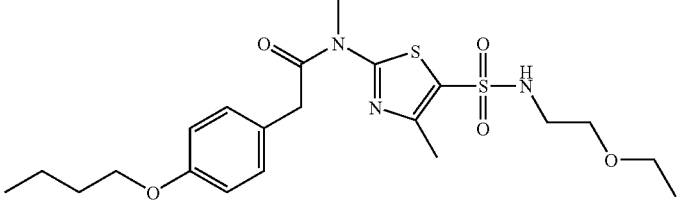 | 68–70 | | |
| 64 | 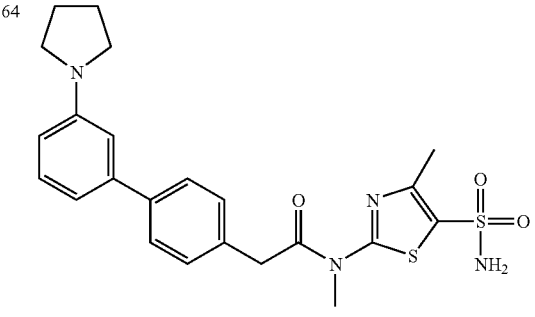 | 152 | | |
| 65 | 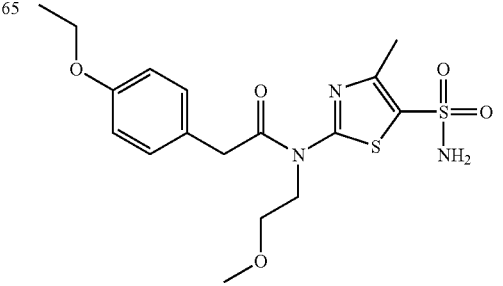 | 165 | | |
| 66 | 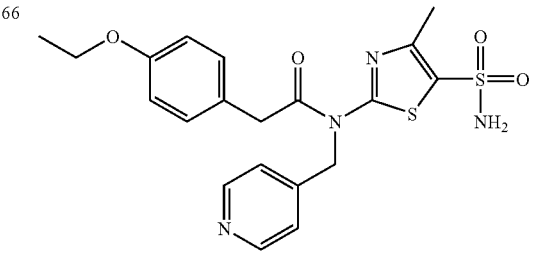 | 122 | | |
| 67 | 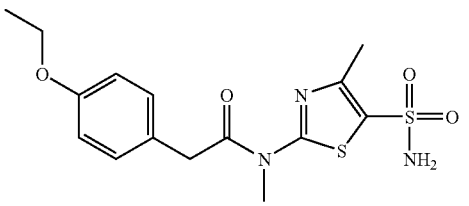 | 168 | | |

| Ex. No. | Structure | M.p. [° C.] | Rf value | Rt [min] method |
|---|---|---|---|---|
| 68 | 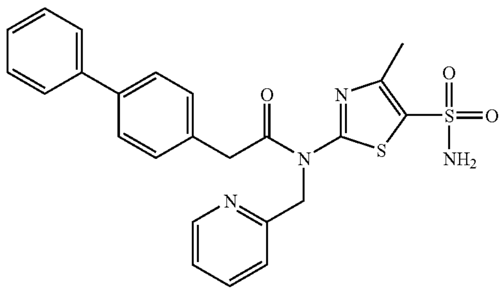 | 205 | | |
| 69 | 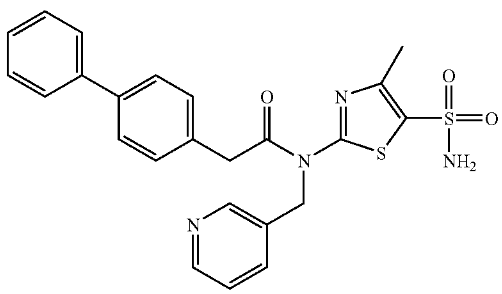 | 189 | | |
| 70 | 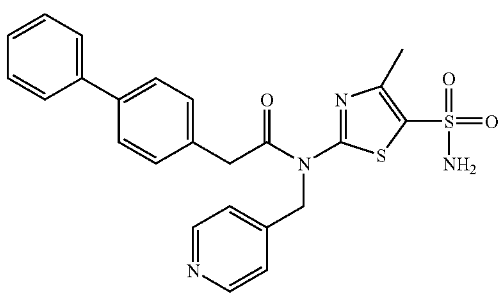 | 130 | | |
| 71 | 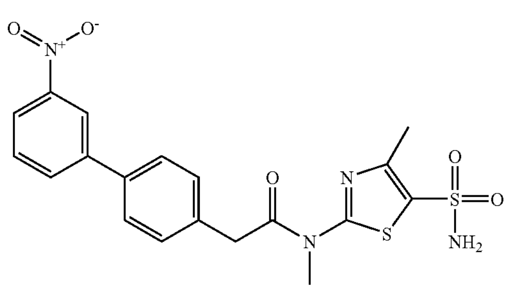 | 202 | | |
| 72 | 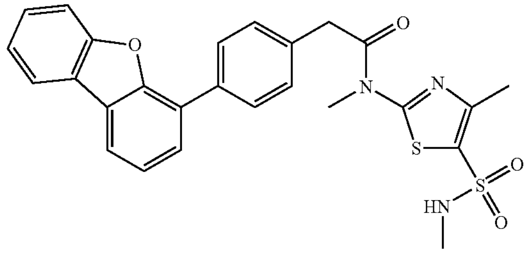 | 109 | | |

-continued

| Ex. No. | Structure | M.p. [° C.] | Rf value | Rt [min] method |
|---|---|---|---|---|
| 73 | 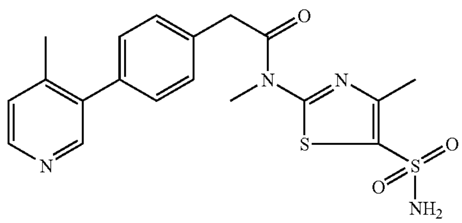 | 204 | | |
| 74 | 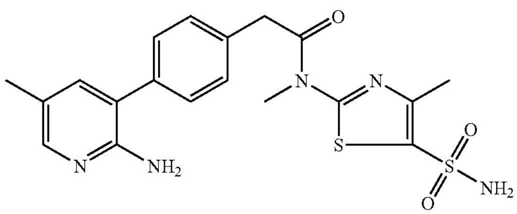 | 183 | | |
| 75 | 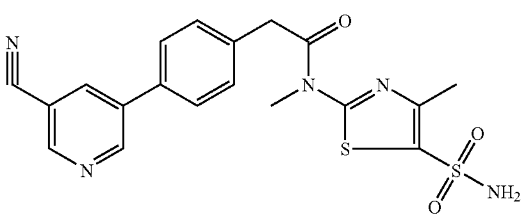 | 231 | | |
| 76 | 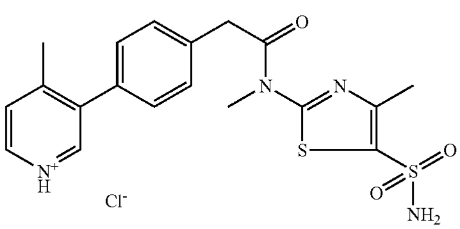 | 234 | | |
| 77 | 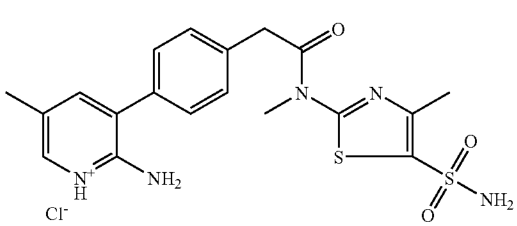 | 230 | | |
| 78 | 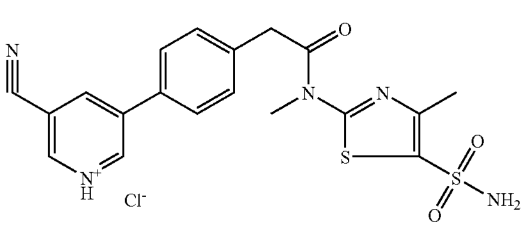 | 232 | | |

-continued

| Ex. No. | Structure | M.p. [° C.] | Rf value | Rt [min] method |
|---|---|---|---|---|
| 79 | 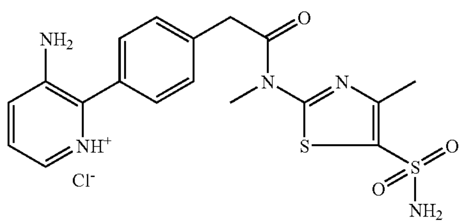 | 264 | | |
| 80 | 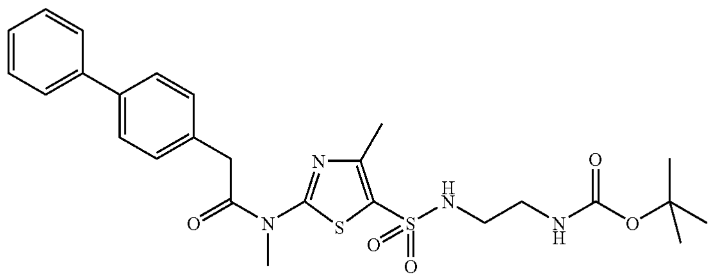 | 150 | | |
| 81 | 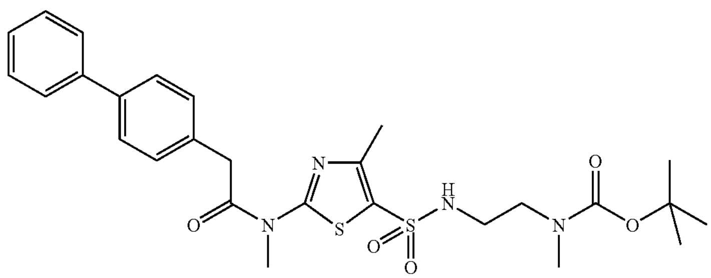 | 175 | | |
| 82 | 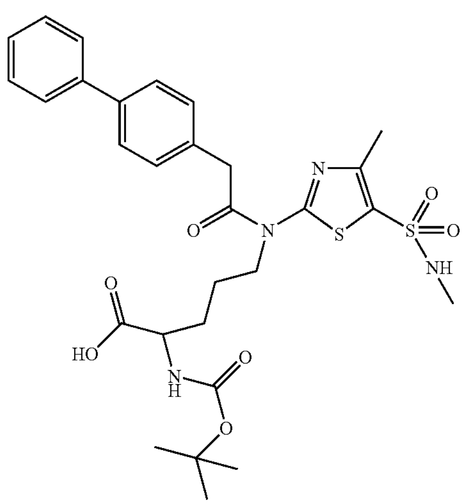 | | 0.13 (CH2Cl2/ MeOH/ NH3 10:1:0.1) | |

-continued
| Ex. No. | Structure | M.p. [° C.] | Rf value | Rt [min] method |
|---|---|---|---|---|
| 83 | 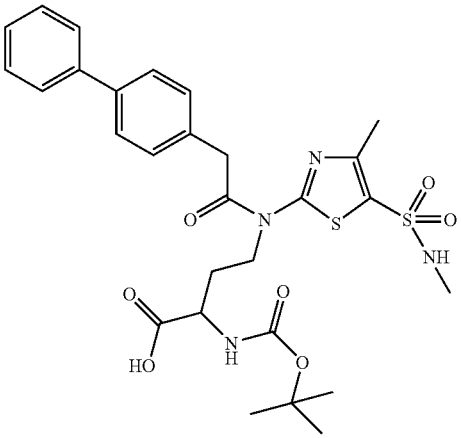 | | 0.10 (CH2Cl2/ MeOH/ NH3 10:1:0.1) | |
| 84 | 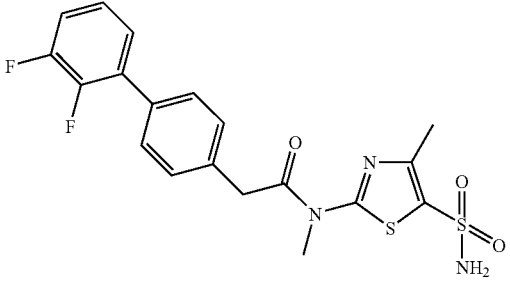 | 202 | | |
| 85 | 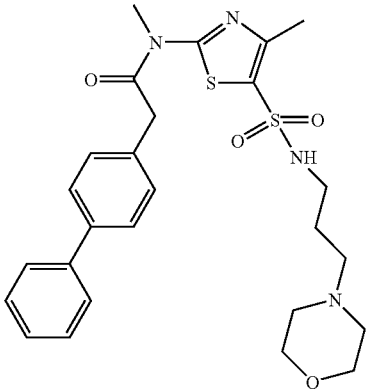 | | | 3.38 |
| 86 | 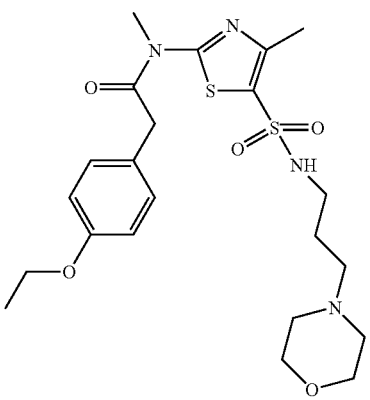 | | | 3.1 |

-continued

| Ex. No. | Structure | M.p. [° C.] | Rf value | Rt [min] method |
|---|---|---|---|---|
| 87 | (2,5-difluorophenyl)-biphenyl-CH2-C(O)-N(CH3)-thiazole(4-Me)-SO2NH2 | 184 | | |
| 88 | (2,6-difluorophenyl)-biphenyl-CH2-C(O)-N(CH3)-thiazole(4-Me)-SO2NH2 | 215 | | |
| 89 | biphenyl-CH2-C(O)-N(CH3)-thiazole(4-Me)-SO2NH-CH2CH2NH2 | 138 | | |
| 90 | [3-(trifluoromethyl)pyridin-2-yl]-phenyl-CH2-C(O)-N(CH3)-thiazole(4-Me)-SO2NHCH3 | 180 | | |
| 91 | (pyrimidin-5-yl)-phenyl-CH2-C(O)-N(CH3)-thiazole(4-Me)-SO2NHCH3 | 193 | | |

-continued
| Ex. No. | Structure | M.p. [° C.] | Rf value | Rt [min] method |
|---|---|---|---|---|
| 92 | 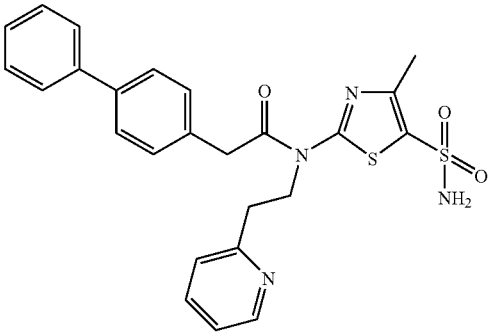 | 136 | | |
| 93 | 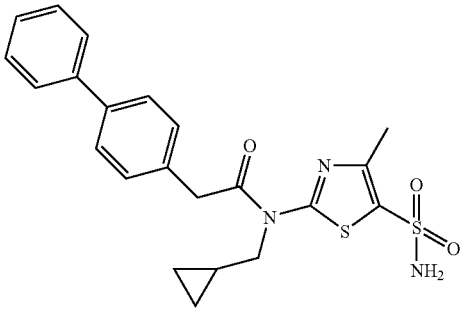 | 161 | | |
| 94 | 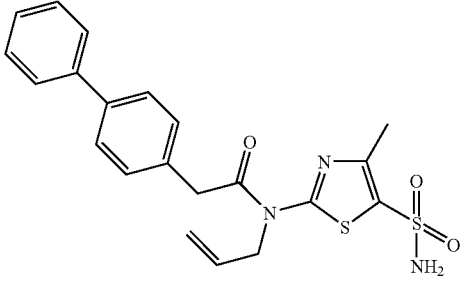 | 117 | | |
| 95 | 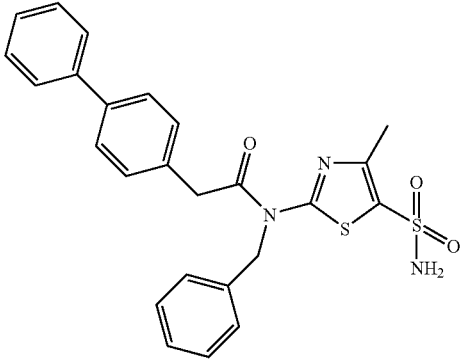 | 154 | | |

-continued

| Ex. No. | Structure | M.p. [° C.] | Rf value | Rt [min] method |
|---|---|---|---|---|
| 96 | 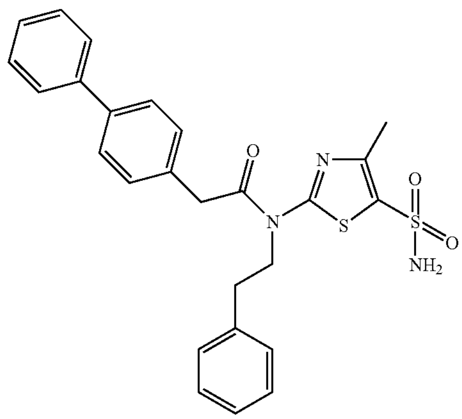 | 174 | | |
| 97 | 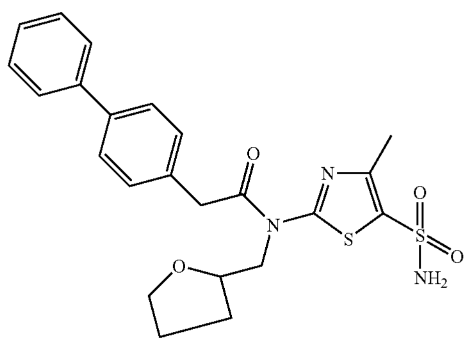 | 159 | | |
| 98 | 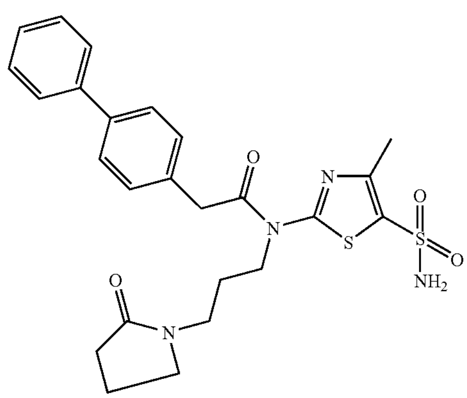 | 203 | | |
| 99 | 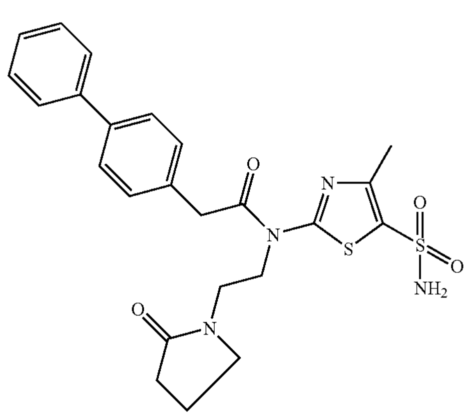 | 202 | | |

-continued
| Ex. No. | Structure | M.p. [° C.] | Rf value | Rt [min] method |
|---|---|---|---|---|
| 100 | 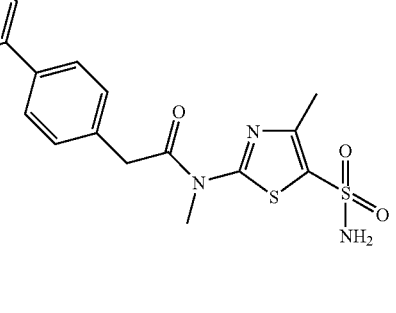 | 209 | | |
| 101 | 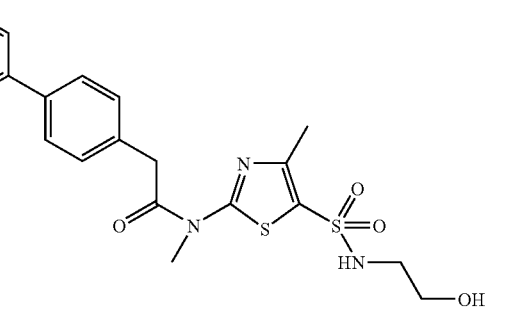 | 167 | | |
| 102 | 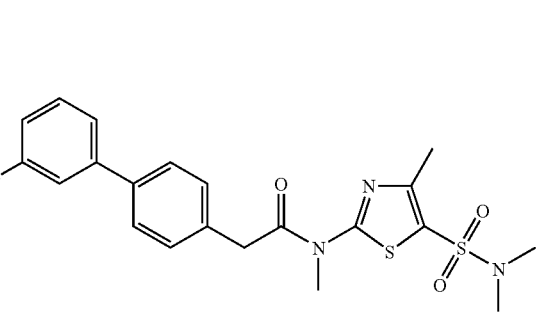 | 81 | | |
| 103 | 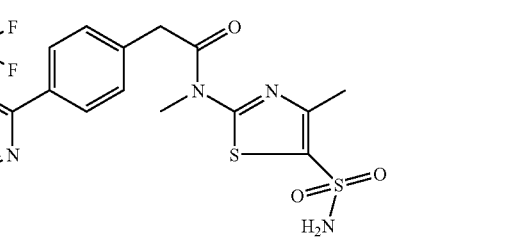 | 221 | | |
| 104 | 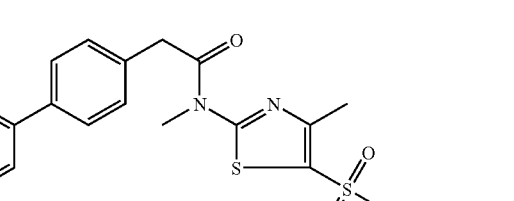 | 234 | | |

-continued

| Ex. No. | Structure | M.p. [° C.] | Rf value | Rt [min] method |
|---|---|---|---|---|
| 105 | 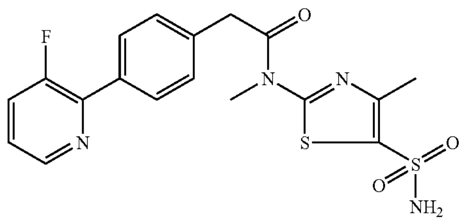 | 218 | | |
| 106 | 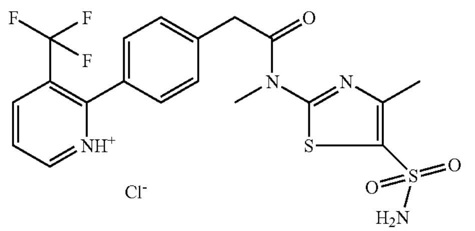 | 225 | | |
| 107 | 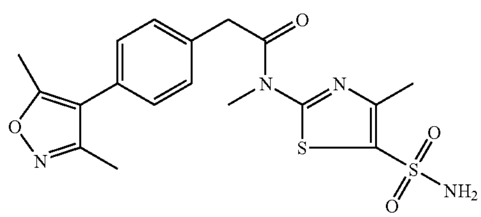 | | 0.38 (CH2Cl2/ MeOH 100:3) | |
| 108 | 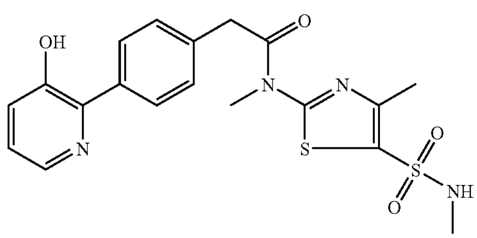 | 225 | | |
| 109 | 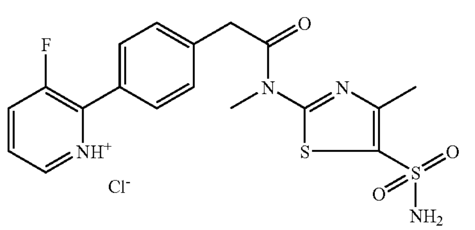 | 206 | | |
| 110 | 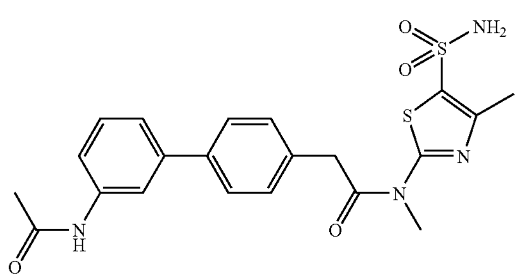 | 234 | | |

-continued

| Ex. No. | Structure | M.p. [° C.] | Rf value | Rt [min] method |
|---|---|---|---|---|
| 112 | 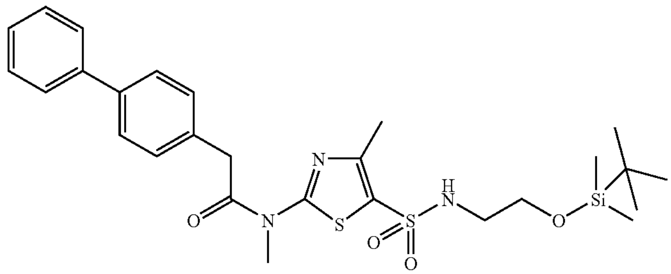 | 128 | | |
| 113 | 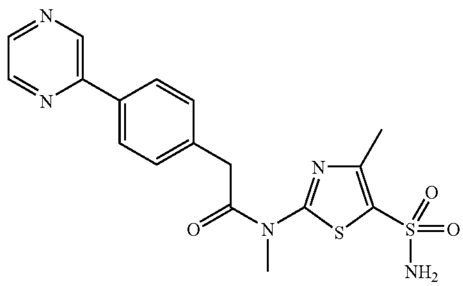 | 217 | | |
| 114 | 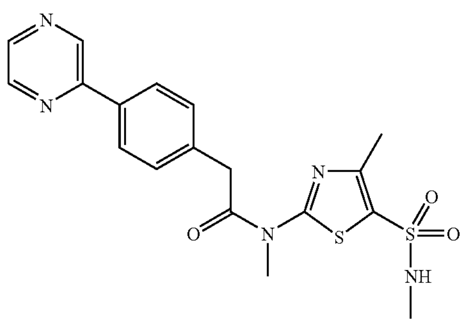 | 187 | | |
| 115 | 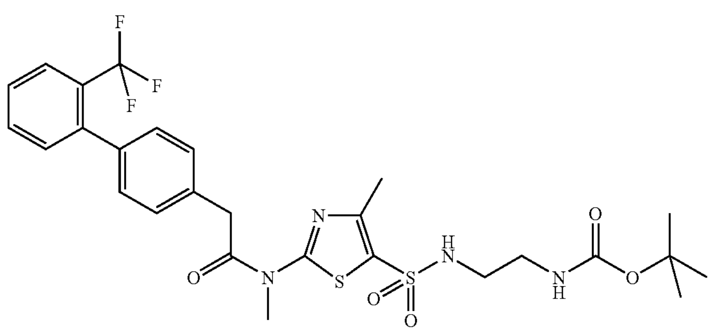 | 156 | | |
| 116 | 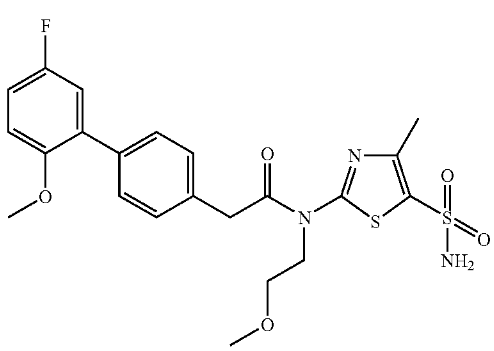 | 199 | | |

-continued

| Ex. No. | Structure | M.p. [° C.] | Rf value | Rt [min] method |
|---|---|---|---|---|
| 117 | 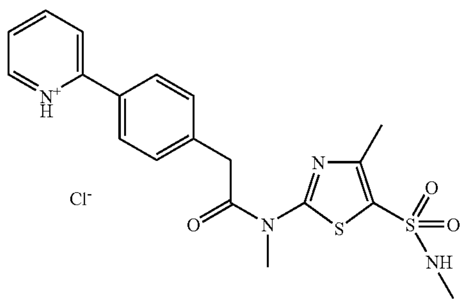 | 237 | | |
| 118 | 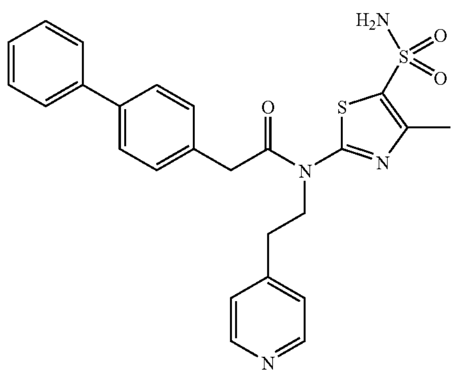 | 204 | | |
| 119 | 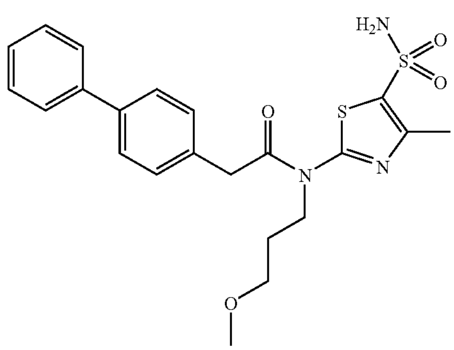 | 148 | | |
| 120 | 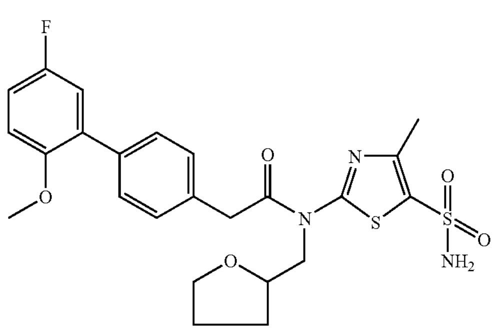 | 79 | | |

-continued

| Ex. No. | Structure | M.p. [° C.] | Rf value | Rt [min] method |
|---|---|---|---|---|
| 121 | 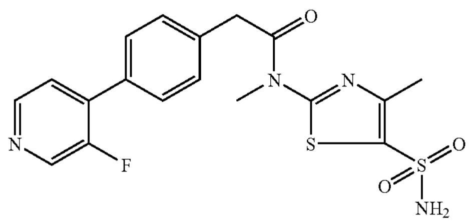 | 223 | | |
| 122 | 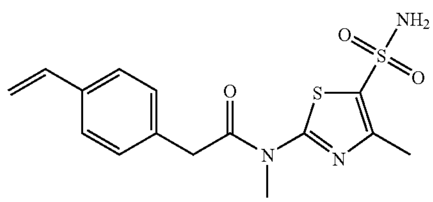 | | 0.50 (CH2Cl2/ MeOH 100:5) | |
| 123 | 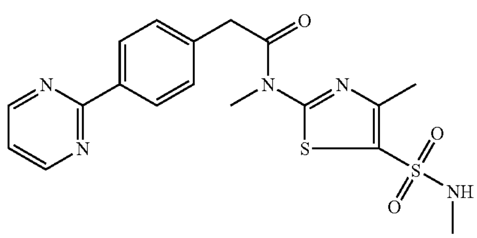 | | 0.57 (CH2Cl2/ MeOH 100:5) | |
| 124 | 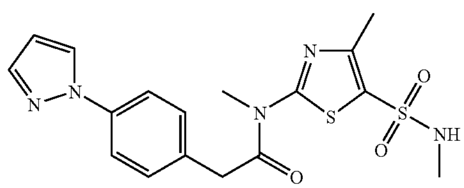 | | | 4.05 |
| 125 | 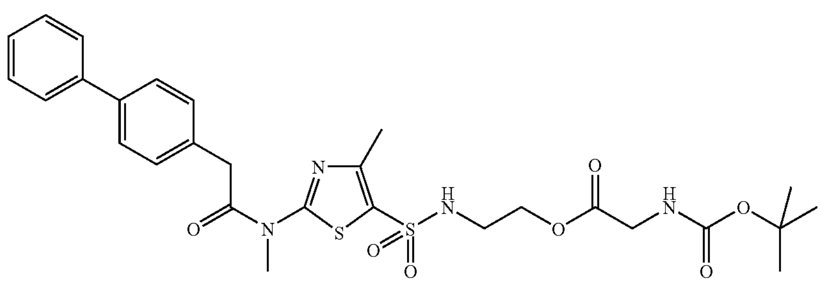 | 159 | | |
| 126 | 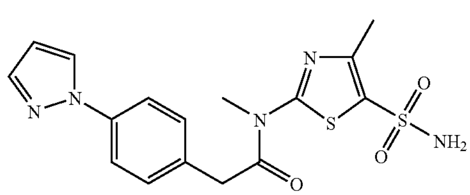 | | | 3.65 |
| 127 | 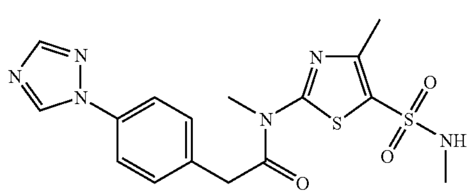 | | | 3.45 |

-continued

| Ex. No. | Structure | M.p. [° C.] | Rf value | Rt [min] method |
|---|---|---|---|---|
| 128 | 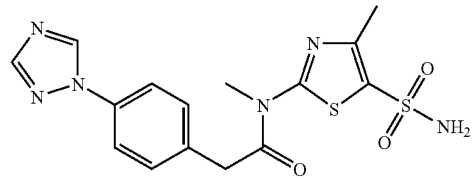 | | | 3.1 |
| 129 | 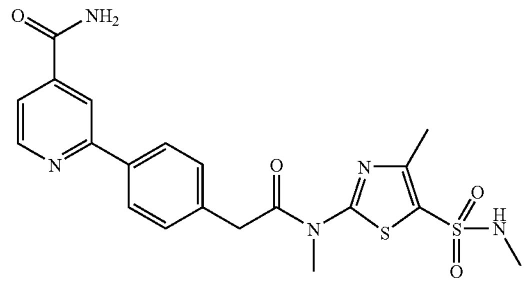 | | 0.14 (CH2Cl2/ MeOH 100:5) | |
| 130 | 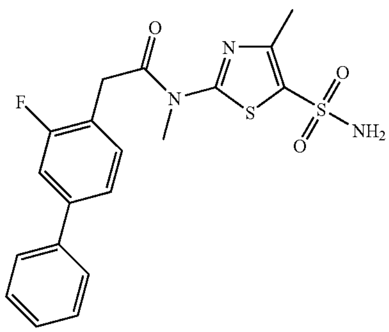 | 130 | | |
| 131 | 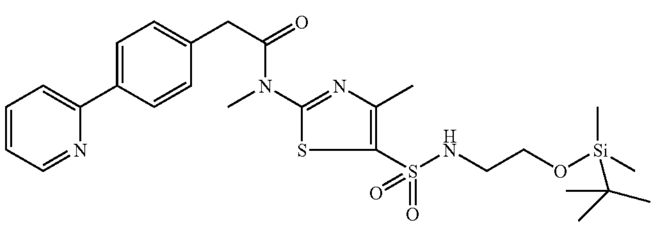 | 130 | | |
| 132 | 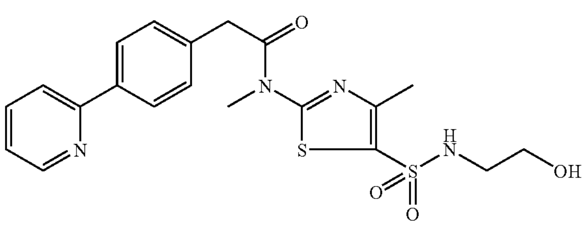 | 175 | | |

In the table above, the Rf value denotes the retention index for silica gel thin-layer chromatography. SMKL-N1-1 denotes the LC-MS method below.

| Method: | SMKL-N1 |
|---|---|
| MS unit type: | Finnigan MAT 900S |
| | Ionization: ESI positive |
| HPLC unit type: | TSP: P4000, AS3000, UV3000HR |
| Pump head: | normal |
| Column: | Symmetry C 18 |

-continued

| | | | | | | |
|---|---|---|---|---|---|---|
| Source: | | 150 mm × 2.1 mm 5 µm Waters | | | | |
| UV detector DAD: | | 210 nm | | | | |
| Oven temp.: | | 40° C. | | | | |
| Gradient: | Time | A:% | B:% | C:% | D:% | Flow |
| | 0 | 10.0 | 45 | 45 | — | 0.6 |
| | 4 | 90 | 5 | 5 | — | 0.6 |
| | 9 | 90 | 5 | 5 | — | 0.6 |

-continued

| | | | | | |
|---|---|---|---|---|---|
| 9.5 | 10.0 | 45 | 45 | — | 0.8 |
| 11.5 | 10.0 | 45 | 45 | — | 0.8 |
| 12 | 10.0 | 45 | 45 | — | 0.6 |

| | |
|---|---|
| A: | $CH_3CN$ |
| B: | HCl 0.01 n |
| C: | $H_2O$ |
| D: | — |

What is claimed is:

1. Compounds of the general formula (I):

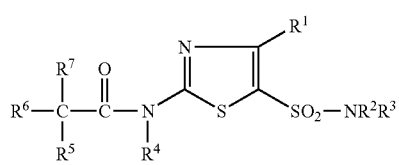

in which $R^1$ represents hydrogen, halogen, $(C_1-C_6)$-alkyl, $(C_1-C_6)$-alkoxy, amino-$(C_{1-C6})$-alkyl or halogeno-$(C_1-C_6)$-alkyl, $R^2$ and $R^3$ are identical or different and represent hydrogen, $(C_1-C_6)$-alkoxy, $(C_3-C_8)$-cycloalkyl or biphenylaminocarbonyl, or represent $(C_1-C_6)$-alkyl which is optionally substituted by 1 to 3 substituents selected from the group consisting of $(C_3-C_6)$-cycloalkyl, $(C_1-C_6)$-alkoxy, halogen, hydroxyl, amino, tri-$(C_1-C_6)$-alkylsilyloxy, radicals of the formula

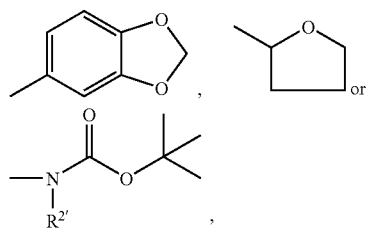

in which $R^{2'}$ represents hydrogen or $(C_1-C_4)$-alkyl, a 5- or 6-membered aromatic heterocycle having up to 3 heteroatoms from the group consisting of S, N and O, where a nitrogen-containing heterocycle may also be attached via the nitrogen atom, a 3- to 8-membered saturated or unsaturated nonaromatic heterocycle having up to 3 heteroatoms from the group consisting of S, N and O, which may optionally be attached via a nitrogen atom, and $(C_6-C_{10})$-aryl which for its part may be substituted by hydroxyl or $(C_1-C_6)$-alkoxy, or represent a group of the formula

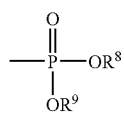

in which $R^8$ and $R^9$ are identical to or different from one another and represent hydrogen and $(C_1-C_4)$-alkyl, or represent a group of the formula

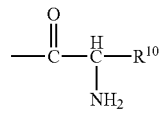

in which $R^{10}$ is the side-group of a naturally occurring α-amino acid, or represent a group of the formula

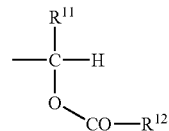

in which $R^{11}$ represents $(C_1-C_4)$-alkyl and $R^{12}$ represents hydrogen, $(C_1-C_4)$-alkyl or represents a group of the formula

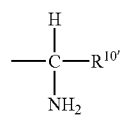

in which $R^{10'}$ is the side-group of a naturally occurring α-amino acid, or $R^2$ and $R^3$ together with the nitrogen atom form a 5- or 6-membered saturated heterocycle which may optionally contain an oxygen atom, $R^4$ represents hydrogen, $(C_1-C_6)$-acyl, $(C_2-C_6)$-alkenyl, $(C_3-C_8)$-cycloalkyl, or $R^4$ represents $(C_1-C_6)$-alkyl which may optionally be substituted by 1 to 3 substituents selected from the group consisting of halogen, hydroxyl, $(C_3-C_8)$-cycloalkyl, $(C_1-C_6)$-acyl, $(C_1-C_6)$-alkoxy, carboxyl,

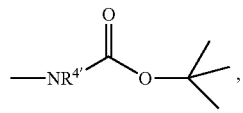

in which $R^{4'}$ represents hydrogen, $-(OCH_2CH_2)_n OCH_2CH_3$, in which n is 0 or 1, phenoxy, $(C_6-C_{10})$-aryl and $-NR^{13}R^{14}$, in which $R^{13}$ and $R^{14}$ are identical or different and represent hydrogen, $(C_1-C_6)$-acyl, $(C_1-C_6)$-alkyl, carbamoyl, mono- or di-$(C_1-C_6)$-alkylamino-$(C_1-C_6)$-alkyl, mono- or di-$(C_1-C_6)$-alkylaminocarbonyl, $(C_6-C_{10})$-aryl or $(C_1-C_6)$-alkoxycarbonyl, or $R^{13}$ and $R^{14}$ together with the nitrogen atom form a 5- or 6-membered saturated heterocycle which may optionally contain a further heteroatom from the group consisting of S and O or a radical of the formula $-NR^{15}$, and which may be substituted by oxo, in which $R^{15}$ represents hydrogen or $(C_1-C_4)$-alkyl, or $R^4$ represents $(C_1-C_6)$-alkyl which is substituted by a 5- or 6-membered aromatic, optionally benzo-fused heterocycle having up to 3 heteroatoms from the group consisting of S, N and O, where a nitrogen-containing heterocycle may also be attached via the nitrogen atom, or which is substituted by radicals of the formulae

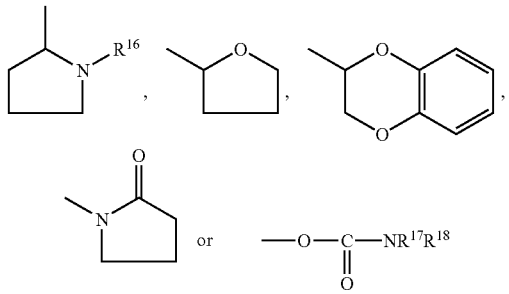

in which $R^{16}$ represents hydrogen or $(C_1-C_6)$-alkyl, $R^{17}$ and $R^{18}$ are identical or different and represent hydrogen, $(C_1-C_6)$alkyl or $(C_6-C_{10})$-aryl, where abovementioned $(C_1-C_6)$-alkyl and $(C_6-C_{10})$-aryl may optionally be substituted by 1 to 3 substituents selected from the group consisting of hydroxyl, $(C_1-C_6)$-alkoxy and halogen, $R^5$ represents hydrogen, $(C_1-C_6)$-alkyl, halogen, amino, mono- or di-$(C_1-C_6)$-alkylamino or represents $(C_1-C_6)$-alkanoylamino, $R^6$ represents phenyl which may optionally be substituted by one to three substituents selected from the group consisting of halogen, $(C_6-C_{10})$-aryl which may optionally be substituted by 1 to 3 substituents selected from the group consisting of $(C_1-C_6)$-alkanoyl, $(C_1-C_6)$-alkoxy, $(C_1-C_6)$-alkyl, halogen, $(C_1-C_6)$-alkoxycarbonyl, nitro, halogeno-$(C_1-C_6)$-alkyl, halogeno-$(C_1-C_6)$-alkoxy, amino, $(C_1-C_6)$-alkylthio, hydroxyl, carboxyl, carbamoyl, mono- or di-$(C_1-C_6)$-alkylaminocarbonyl, mono- or di-$(C_1-C_6)$-alkanoylamino, $(C_1-C_6)$-alkoxycarbonylamino, $(C_1-C_6)$-alkylsulphoxy, $(C_1-C_6)$-alkylsulphonyl, tri-$(C_1-C_6)$-alkylsilyloxy, a 3- to 8-membered saturated or unsaturated nonaromatic mono- or bicyclic heterocycle having up to 3 heteroatoms from the group consisting of S, N and O, which may optionally be attached via a nitrogen atom, and/or cyano, $(C_1-C_6)$-alkoxy, $(C_1-C_6)$-alkoxycarbonyl, $(C_1-C_6)$-alkylthio, hydroxyl, carboxyl, partially fluorinated $(C_1-C_6)$-alkoxy having up to 6 fluorine atoms, $(C_1-C_6)$-alkyl which is optionally substituted by a radical of the formula

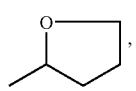

a 5- or 6-membered aromatic heterocycle having up to 3 heteroatoms from the group consisting of S, N and O which may optionally be attached via a nitrogen atom and which may optionally be substituted by 1 to 3 substituents selected from the group consisting of $(C_1-C_6)$-alkanoyl, $(C_1-C_6)$-alkoxy, $(C_1-C_6)$-alkyl, halogen, $(C_1-C_6)$-alkoxycarbonyl, nitro, halogeno-$(C_1-C_6)$-alkyl, halogeno-$(C_1-C_6)$-alkoxy, amino, $(C_1-C_6)$-alkylthio, hydroxyl, carboxyl, carbamoyl, aminocarbonyl, mono- or di-$(C_1-C_6)$-alkylaminocarbonyl, mono- or di-$(C_1-C_6)$-alkanoylamino, $(C_1-C_6)$-alkoxycarbonylamino, $(C_1-C_6)$-alkylsulphoxy, $(C_1-C_6)$-alkylsuphonyl, a 3- to 8-membered saturated or unsaturated nonaromatic mono- or bicyclic heterocycle having up to 3 heteroatoms from the group consisting of S, N and O which may optionally be attached via a nitrogen atom, and/or cyano, a 3- to 8-membered saturated or unsaturated non-aromatic mono- or bicyclic heterocycle having up to 3 heteroatoms from the group consisting of S, N and O, which may optionally be attached via a nitrogen atom and which may optionally be substituted by 1 to 3 substituents selected from the group consisting of oxo, halogen, hydroxyl, $(C_1-C_6)$-alkoxycarbonyl, $(C_1-C_6)$-alkoxycarbonylamino, $(C_1-C_6)$-alkyl, halogeno-$(C_1-C_6)$-alkyl and hydroxy-$(C_1-C_6)$-alkyl, $(C_2-C_6)$-alkenyl and groups of the formulae

—$OR^{19}$,

—$NR^{20}R^{21}$ or —$CO$—$NR^{22}R^{23}$, carbazole, dibenzofuran or dibenzothiophene, xanthene or 9,10-dihydroacridine, in which $R^{19}$ is phenyl which for its part is optionally substituted by a group of the formula —$NR^{24}R^{25}$ in which $R^{24}$ and $R^{25}$ are identical or different and represent hydrogen, $(C_1-C_6)$-alkyl or $(C_1-C_6)$-acyl, or $R^{19}$ represents $(C_1-C_6)$-alkyl which is optionally mono- to trisubstituted by hydroxyl and/or halogen, $R^{20}$ and $R^{21}$ are identical or different and represent hydrogen, carbamoyl, mono- or di-$(C_1-C_6)$-alkylaminocarbonyl, phenyl, $(C_1-C_6)$-acyl or $(C_1-C_6)$-alkyl, where abovementioned $(C_1-C_6)$-alkyl is optionally substituted by $(C_1-C_6)$-alkoxy, $(C_1-C_6)$-acyl, by phenyl or by a 5- or 6-membered aromatic heterocycle having up to 3 heteroatoms from the group consisting of S, N and O, where abovementioned phenyl and abovementioned aromatic heterocycle are optionally mono- to trisubstituted by identical or different substituents from the group consisting of halogen and hydroxyl, and $R^{22}$ and $R^{23}$ are identical or different and represent hydrogen or $(C_1-C_6)$-alkyl, and $R^7$ may have the meaning of $R^5$ and may be identical to or different from $R^5$, and their salts.

2. Compounds of the general formula (I) according to claim 1:

$$R^6-\underset{R^5}{\underset{|}{\overset{R^7}{\overset{|}{C}}}}-\overset{O}{\overset{\|}{C}}-\underset{R^4}{\overset{}{N}}-\underset{S}{\overset{N}{\underset{\|}{\diagdown}}}\overset{R^1}{\underset{SO_2-NR^2R^3}{\diagup}} \qquad (I)$$

in which $R^1$ represents hydrogen, halogen, $(C_1-C_6)$-alkyl, $(C_1-C_6)$-alkoxy, amino-$(C_1-C_6)$-alkyl or halogeno-$(C_1-C_6)$-alkyl, $R^2$ and $R^3$ are identical or different and represent hydrogen, $(C_1-C_6)$-alkoxy, $(C_3-C_8)$-cycloalkyl or biphenylaminocarbonyl, or represent $(C_1-C_6)$-alkyl which is optionally substituted by 1 to 3 substituents selected from the group consisting of $(C_3-C_6)$-cycloalkyl, $(C_1-C_6)$-alkoxy, halogen, hydroxyl, amino, radicals of the formula

[structure: methylenedioxyphenyl] or [structure: tetrahydrofuranyl] , a 5- or 6-membered aromatic heterocycle having up to 3 heteroatoms from the group consisting of S, N and O, where a nitrogen-containing heterocycle may also be attached via the nitrogen atom, a 3- to 8-membered saturated or unsaturated nonaromatic heterocycle having up to 3 heteroatoms from the group consisting of S, N and O, which may optionally be attached via a nitrogen atom, and $(C_6-C_{10})$-aryl, which for its part may be substituted by hydroxyl or $(C_1-C_6)$-alkoxy, or represent a group of the formula $$-\underset{OR^9}{\overset{O}{\underset{\|}{\overset{\|}{P}}}}-OR^8$$

in which $R^8$ and $R^9$ are identical to or different from one another and represent hydrogen and $(C_1-C_4)$-alkyl, or represent a group of the formula $$-\overset{O}{\overset{\|}{C}}-\underset{NH_2}{\overset{H}{\underset{|}{C}}}-R^{10}$$

in which $R^{10}$ is the side-group of a naturally occurring α-amino acid, or represent a group of the formula $$-\underset{O\diagdown_{CO-R^{12}}}{\overset{R^{11}}{\underset{|}{C}}}-H$$

in which $R^{11}$ represents $(C_1-C_4)$-alkyl and $R^{12}$ represents hydrogen, $(C_1-C_4)$-alkyl or represents a group of the formula $$-\underset{NH_2}{\overset{H}{\underset{|}{C}}}-R^{10'}$$

in which $R^{10'}$ is the side-group of a naturally occurring α-amino acid, or $R^2$ and $R^3$ together with the nitrogen atom form a 5- or 6-membered saturated heterocycle which may optionally contain an oxygen atom, $R^4$ represents hydrogen, $(C_1-C_6)$-acyl, $(C_2-C_6)$-alkenyl, $(C_3-C_8)$-cycloalkyl, or $R^4$ represents $(C_1-C_6)$-alkyl which may optionally be substituted by 1 to 3 substituents selected from the group consisting of halogen, hydroxyl, $(C_1-C_6)$-acyl, $(C_1-C_6)$alkoxy, —$(OCH_2CH_2)_nOCH_2CH_3$, in which n is 0 or 1, phenoxy, $(C_6-C_{10})$-aryl and —$NR^3R^{14}$, in which $R^{13}$ and $R^{14}$ are identical or different and represent hydrogen, $(C_1-C_6)$-acyl, $(C_1-C_6)$-alkyl, carbamoyl, mono- or di-$(C_1-C_6)$-alkylamino-$(C_1-C_6)$-alkyl, mono- or di-$(C_1-C_6)$-alkylaminocarbonyl, $(C_6-C_{10})$-aryl or $(C_1-C_6)$-alkoxycarbonyl, or $R^{13}$ and $R^{14}$ together with the nitrogen atom form a 5- or 6-membered saturated heterocycle which may optionally contain a further heteroatom from the group consisting of S and O or a radical of the formula —$NR^{15}$ and which may be substituted by oxo, in which $R^{15}$ represents hydrogen or $(C_1-C_4)$-alkyl, or $R^4$ represents $(C_1-C_6)$-alkyl which is substituted by a 5- or 6-membered aromatic, optionally benzo-fused heterocycle having up to 3 heteroatoms from the group consisting of S, N and O, where a nitrogen-containing heterocycle may also be attached via the nitrogen atom, or which is substituted by radicals of the formulae

[structure: pyrrolidinyl with $R^{16}$], [structure: tetrahydrofuranyl], [structure: benzodioxanyl] or $$-O-\overset{O}{\overset{\|}{C}}-NR^{17}R^{18}$$

in which $R^{16}$ represents hydrogen or $(C_1-C_6)$-alkyl, $R^{17}$ and $R^{18}$ are identical or different and represent hydrogen, $(C_1-C_6)$-alkyl or $(C_6-C_{10})$-aryl, where abovementioned $(C_1-C_6)$-alkyl and $(C_6-C_{10})$-aryl may optionally be substituted by 1 to 3 substituents selected from the group consisting of hydroxyl, $(C_1-C_6)$-alkoxy and halogen, $R^5$ represents hydrogen, $(C_1-C_6)$-alkyl, halogen, amino, mono- or di-$(C_1-C_6)$-alkylamino or represents $(C_1-C_6)$-alkanoylamino, $R^6$ represents phenyl which may optionally be substituted by one to three substituents selected from the group consisting of halogen, $(C_6-C_{10})$-aryl which may optionally be substituted by 1 to 3 substituents selected from the group consisting of $(C_1-C_6)$-alkanoyl, $(C_1-C_6)$-alkoxy, $(C_1-C_6)$-alkyl, halogen, $(C_1-C_6)$-alkoxycarbonyl, nitro, halogeno-$(C_1-C_6)$-alkyl, halogeno-$(C_1-C_6)$-alkoxy, amino, $(C_1-C6)$-alkylthio, hydroxyl, carboxyl, carbamoyl, mono- or di-$(C_1-C_6)$-alkylaminocarbonyl, mono- or di-$(C_1-C_6)$-alkanoylamino, $(C_1-C_6)$-alkoxycarbonylamino, $(C_1-C_6)$-alkylsulphoxy, $(C_1-C_6)$-alkylsulphonyl, tri-$(C_1-C_6)$-alkylsilyloxy, a 3- to 8-membered saturated or unsaturated nonaromatic mono- or bicyclic heterocycle having up to 3 heteroatoms from the group consisting of S, N and O, which may optionally be attached via a nitrogen atom, and/or cyano, $(C_1-C_6)$-alkoxy, $(C_1-C_6)$-alkoxycarbonyl, $(C_1-C_6)$-alkylthio, hydroxyl, carboxyl, partially fluorinated $(C_1-C_6)$-alkoxy having up to 6 fluorine atoms, $(C_1-C_6)$-alkyl which is optionally substituted by a radical of the formula

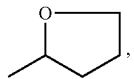

a 5- or 6-membered aromatic heterocycle having up to 3 heteroatoms from the group consisting of S, N and O which may optionally be attached via a nitrogen atom and which may optionally be substituted by 1 to 3 substituents selected from the group consisting of $(C_1-C_6)$-alkanoyl, $(C_1-C_6)$-alkoxy, $(C_1-C_6)$-alkyl, halogen, $(C_1-C_6)$-alkoxycarbonyl, nitro, halogeno-$(C_1-C_6)$-alkyl, halogeno-$(C_1-C_6)$-alkoxy, amino, $(C_1-C_6)$-alkylthio, hydroxyl, carboxyl, carbamoyl, mono- or di-$(C_1-C_6)$-alkylaminocarbonyl, mono- or di-$(C_1-C_6)$ alkanoylamino, $(C_1-C_6)$-alkoxycarbonylamino, $(C_1-C_6)$-alkylsulphoxy, $(C_1-C_6)$-alkylsuphonyl, a 3- to 8-membered saturated or unsaturated nonaromatic mono- or bicyclic heterocycle having up to 3 heteroatoms from the group consisting of S, N and O which may optionally be attached via a nitrogen atom, and/or cyano, a 3- to 8-membered saturated- or unsaturated nonaromatic mono- or bicyclic heterocycle having up to 3 heteroatoms from the group consisting of S, N and O, which may optionally be attached via a nitrogen atom and which may optionally be substituted by 1 to 3 substituents selected from the group consisting of oxo, halogen, hydroxyl, $(C_1-C_6)$-alkoxycarbonyl, $(C_1-C_6)$-alkoxycarbonylamino, $(C_1-C_6)$-alkyl, halogeno-$(C_1-C_6)$-alkyl and hydroxy-$(C_1-C_6)$-alkyl, $(C_2-C_6)$-alkenyl and groups of the formulae

—$OR^{19}$,

—$NR^{20}R^{21}$ or —CO—$NR^{22}R^{23}$, in which $R^{19}$ is phenyl which for its part is optionally substituted by a group of the formula —$NR^{24}R^{25}$, in which $R^{24}$ and $R^{25}$ are identical or different and represent hydrogen, $(C_1-C_6)$-alkyl or $(C_1-C_6)$-acyl, or $R^{19}$ represents $(C_1-C_6)$-alkyl which is optionally mono- to trisubstituted by hydroxyl and/or halogen, $R^{20}$ and $R^{21}$ are identical or different and represent hydrogen, carbamoyl, mono- or di-$(C_1-C_6)$-alkylaminocarbonyl, phenyl, $(C_1-C_6)$-acyl or $(C_1-C_6)$-alkyl, where abovementioned $(C_1-C_6)$-alkyl is optionally substituted by $(C_1-C_6)$-alkoxy, $(C_1-C_6)$-acyl, by phenyl or by a 5- or 6-membered aromatic heterocycle having up to 3 heteroatoms from the group consisting of S, N and O, where abovementioned phenyl and abovementioned aromatic heterocycle are optionally mono- to trisubstituted by identical or different substituents from the group consisting of halogen and hydroxyl, and $R^{22}$ and $R^{23}$ are identical or different and represent hydrogen or $(C_1-C_6)$-alkyl, and $R^7$ may have the meaning of $R^5$ and may be identical to or different from $R^5$, and their salts.

3. Compounds of the general formula (I) according to claim 1 or 2, in which $R^1$ represents hydrogen or $(C_1-C_6)$-alkyl.

4. Compounds of the general formula (I) according to claim 1, in which $R^2$ and $R^3$ each independently represent hydrogen or $(C_1-C_6)$-alkyl.

5. Compounds of the general formula (I) according to claim 1, in which $R^4$ represents hydrogen or $(C_1-C_6)$-alkyl.

6. Compounds of the general formula (I) according to claim 1, in which $R^5$ represents hydrogen.

7. Compounds of the general formula (I) according to claim 1, in which $R^6$ represents phenyl which may optionally be substituted by one to three substituents selected from the group consisting of halogen, $(C_6-C_{10})$-aryl which may optionally be substituted by 1 to 3 substituents selected from the group consisting of $(C_1-C_6)$-alkanoyl, $(C_1-C_6)$-alkoxy, $(C_1-C_6)$-alkyl, halogen, $(C_1-C_6)$-alkoxycarbonyl, nitro, halogeno-$(C_1-C_6)$-alkyl, halogeno-$(C_1-C_6)$-alkoxy, amino, hydroxyl, mono- or di-$(C_1-C_6)$-alkylamino, mono- or di-$(C_1-C_6)$-alkanoylamino, $(C_1-C_6)$-alkoxycarbonylamino, and/or cyano, and a 5- or 6-membered aromatic heterocycle having up to 3 heteroatoms from the group consisting of S, N and O, which may optionally be attached via a nitrogen atom.

8. Compounds according to claim 1 having the following formula:

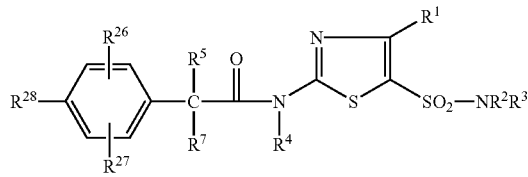

in which $R^1$, $R^2$, $R^3$, $R^4$, $R^5$ and $R^7$ are each as defined in claim 1, $R^{26}$ and $R^{27}$ are identical or different and represent hydrogen, halogen, $(C_1-C_6)$-alkoxy, $(C_1-C_6)$-alkoxycarbonyl, $(C_1-C_6)$-alkylthio, hydroxyl, carboxyl, partially fluorinated $(C_1-C_6)$-alkoxy having up to 6 fluorine atoms, $(C_1-C_6)$-alkyl, a group of the formulae —$OR^9$, —$NR^{20}R^{21}$ or —CO—N $R^{22}R^{23}$, in which $R^{19}$ represents phenyl which for its part is optionally substituted by a group of the formula —$NR^{24}R^{25}$, in which $R^{24}$ and $R^{25}$ are identical or different and represent hydrogen, $(C_1-C_6)$-alkyl or $(C_1-C_6)$-acyl, or $R^{19}$ represents $(C_1-C_6)$-alkyl which is optionally mono- to trisubstituted by hydroxyl and/or halogen, $R^{20}$ and $R^{21}$ are identical or different and represent hydrogen, carbamoyl, mono- or di-$(C_1-C_6)$-alkylaminocarbonyl, phenyl, $(C_1-C_6)$-acyl or $(C_1-C_6)$-alkyl, where abovementioned $(C_1-C_6)$-alkyl is optionally substituted by $(C_1-C_6)$-alkoxy, $(C_1-C_6)$-acyl, phenyl or by a 5- or 6-membered aromatic heterocycle having up to 3 heteroatoms from the group consisting of S, N and O, where abovementioned phenyl and abovementioned aromatic heterocycle are optionally mono- to trisubstituted by identical or different substituents from the group consisting of halogen and hydroxyl, and $R^{22}$ and $R^{23}$ are identical or different and represent hydrogen or $(C_1-C_6)$-alkyl, $R^{28}$ represents $(C_6-C_{10})$-aryl, which may optionally be substituted by 1 to 3 substituents selected from the group consisting of $(C_1-C_6)$-alkanoyl, $(C_1-C_6)$-alkoxy, $(C_1-C_6)$-alkyl, halogen, $(C_1-C_6)$-alkoxycarbonyl, nitro, halogen-$(C_1-C_6)$-alkyl, halogen-$(C_1-C_6)$-alkoxy, amino, $(C_1-C_6)$-alkylthio, hydroxyl, carboxyl, carbamoyl, mono- or di-$(C_1-C_6)$-alkylaminocarbonyl, mono- or di-$(C_1-C_6)$-alkanoylamino, $(C_1-C_6)$-alkoxycarbonylamino, $(C_1-C_6)$-alkylsulphoxy, $(C_1-C_6)$-alkylsulphonyl, tri-$(C_1-C_6)$-alkylsilyloxy, a 3- to 8-membered saturated or unsaturated nonaromatic mono- or bicyclic heterocycle having up to 3 heteroatoms from the group consisting of S, N and O, which may optionally be attached via a nitrogen atom, and/or cyano, or $R^{28}$ represents a 5- or 6-membered aromatic heterocycle having up to 3 heteroatoms from the group consisting of S, N and O, which may optionally be attached via a nitrogen atom and which may optionally be substituted by 1 to 3 substituents selected from the group consisting of $(C_1-C_6)$-alkanoyl, $(C_1-C_6)$-alkoxy, $(C_1-C_6)$-alkyl, halogen, $(C_1-C_6)$-alkoxycarbonyl, nitro, halogeno-$(C_1-C_6)$-alkyl, halogeno-$(C_1-C_6)$-alkoxy, amino, $(C_1-C_6)$-alkylthio, hydroxyl, carboxyl, carbamoyl, mono- or di-$(C_1-C_6)$-alkylaminocarbonyl, mono- or di-$(C_1-C_6)$-alkanoylamino, $(C_1-C_6)$-alkoxycarbonylamino, $(C_1-C_6)$-alkylsulphoxy, $(C_1-C_6)$-alkylsulphonyl, a 3- to 8-membered saturated or unsaturated nonaromatic mono- or bicyclic heterocycle having up to 3 heteroatoms from the group consisting of S, N and O, which may optionally be attached via a nitrogen atom, and/or cyano, and their salts.

9. Compound according to claim 1 of the formula:

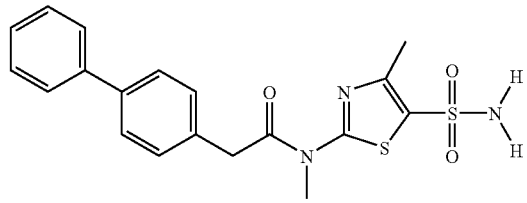

and pharmaceutically acceptable salts thereof.

10. Compound according to claim 1 of the formula:

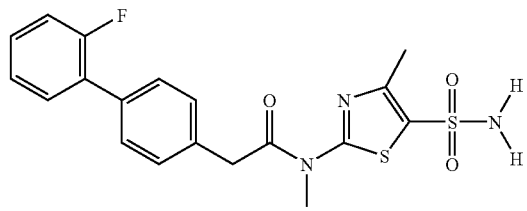

and pharmaceutically acceptable salts thereof.

11. Compound according to claim 1 of the formula:

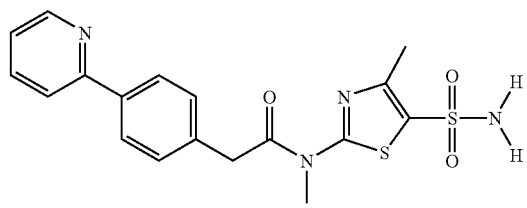

and pharmaceutically acceptable salts thereof.

12. Compound according to claim 1 of the formula:

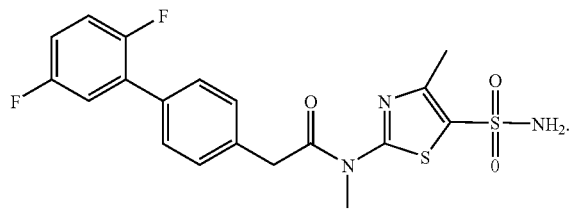

13. Compound according to claim 1 of the formula:

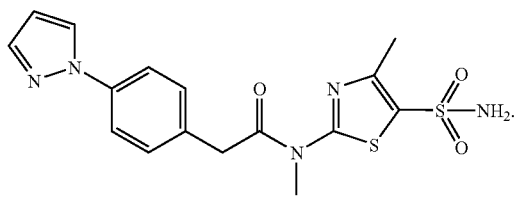

14. Compounds of the general formula (IV)

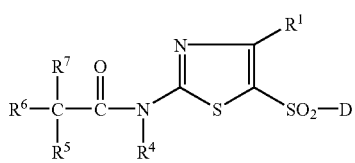
(IV)

in which $R^1$, $R^4$, $R^5$, $R^6$ and $R^7$ are each as defined in claim 1 and D is a halogen atom.

15. Process for preparing the compounds of the general formula (I) according to claim 1, characterized in that
[A] compounds of the general formula (II)

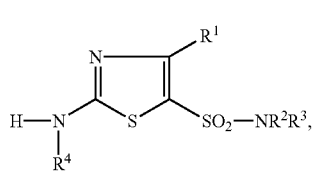
(II)

in which
$R^1$, $R^2$, $R^3$ and $R^4$ are each as defined in claim 1,
are reacted with compounds of the general formula (III)

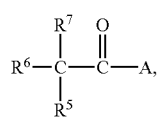
(III)

in which
A represents a leaving group and
$R^5$, $R^6$ and $R^7$ are each as defined in claim 1,
in inert solvents,
or
[B] compounds of the general formula (IV)

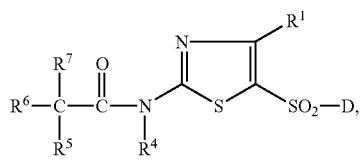
(IV)

in which
$R^1$, $R^4$, $R^5$, $R^6$ and $R^7$ are each as defined in claim 1 and D is a halogen atom,
are reacted with amines of the general formula (V), $HNR^2R^3$     (V)

in which $R^2$ and $R^3$ are each as defined in claim 1,
in inert solvents,
or
[C] compounds of the general formula (X)

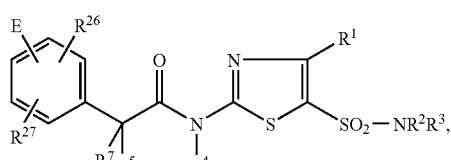
(X)

in which $R^1$, $R^2$, $R^3$, $R^4$, $R^5$, and $R^7$ are each as defined in claim 1,
$R^{26}$ and $R^{27}$ are identical or different and represent hydrogen, halogen, $(C_1-C_6)$-alkoxy, $(C_1-C_6)$-alkoxycarbonyl, $(C_1-C_6)$-alkylthio, hydroxyl, carboxyl, partially fluorinated $(C_1-C_6)$-alkoxy having up to 6 fluorine atoms, $(C_1-C_6)$-alkyl, a group of the formulae $-OR^{19}$, $-NR^{20}R^{21}$ or $-CO-NR^{22}R^{23}$, in which
$R^{19}$ represents phenyl which for its part is optionally substituted by a group of the formula $-NR^{24}R^{25}$, in which $R^{24}$ and $R^{25}$ are identical or different and represent hydrogen $(C_1-C_6)$ or $(C_1-C_6)$-acyl, or
$R^{19}$ represents $(C_1-C_6)$-alkyl which is optionally mono- to trisubstituted by hydroxyl and/or halogen,
$R^{20}$ and $R^{21}$ are identical or different and represent hydrogen, carbamoyl, mono- or di-$(C_1-C_6)$-alkylaminocarbonyl, phenyl, $(C_1-C_6)$-acyl or $(C_1-C_6)$alkyl, where abovementioned $(C_1-C_6)$-alkyl is optionally substituted by $(C_1-C_6)$-alkoxy, $(C_1-C_6)$-acyl, phenyl or by a 5- or 6-membered aromatic heterocycle having up to 3 heteroatoms from the group consisting of S. N and O,
where abovementioned phenyl and abovementioned aromatic heterocycle are optionally mono- to trisubstituted by identical or different substituents from the group consisting of halogen and hydroxyl, and
$R^{22}$ and $R^{23}$ are identical or different and represent hydrogen or $(C_1-C_6)$-alkyl,
and E is trifluoromethanesulphonate or halogen,
are reacted with boronic acids or stannanes of the general formula (XI):

$R^{28}M$     (XI), in which
$R^{28}$ represents $(C_6-C_{10})$-aryl, which may optionally be substituted by 1 to 3 substituents selected from the group consisting of $(C_1-C_6)$-alkanoyl, $(C_1-C_6)$-alkoxy, $(C_1-C_6)$-alkyl, halogen, $(C_1-C_6)$-alkoxycarbonyl, nitro, halogen-$(C_1-C_6)$-alkyl, halogen-$(C_1-C_6)$-alkoxy, amino, $(C_1-C_6)$-alkylthio, hydroxyl, carboxyl, carbamoyl, mono- or di-$(C_1-C_6)$-alkylaminocarbonyl, mono- or di-$(C_1-C_6)$-alkanoylamino, $(C_1-C_6)$-alkoxycarbonylamino, $(C_1-C_6)$-alkylsulphoxy, $(C_1-C_6)$-alkylsulphonyl. tri-$(C_1-C_6)$-alkylsilyloxy, a 3- to 8-membered saturated or unsaturated nonaromatic mono- or bicyclic heterocycle having up to 3 heteroatoms from the group consisting of S, N and O, which may optionally be attached via a nitrogen atom, and/or cyano, or $R^{28}$ represents a 5- or 6-membered aromatic heterocycle having up to 3 heteroatoms from the group consisting of S, N and O, which may optionally be attached via a nitrogen atom and which may optionally be substituted by 1 to 3 substituents selected from the group consisting of $(C_1-C_6)$-alkanoyl $(C_1-C_6)$-alkoxy, $(C_1-C_6)$-alkyl, halogen, $(C_1-C_6)$-alkoxycarbonyl, nitro, halogeno-$(C_1-C_6)$alkyl, halogeno-$(C_1-C_6)$-alkoxy, amino, $(C_1-C_6)$-alkylthio, hydroxyl, carboxyl, carbamoyl, mono- or di-$(C_1-C_6)$-alkylaminocarbonyl, mono- or di-$(C_1-C_6)$-alkanoylamino, $(C_1-C_6)$-alkoxycarbonylamino, $(C_1-C_6)$-alkylsulphoxy, $(C_1-C_6)$-alkylsulphonyl, a 3- to 8-membered saturated or unsaturated nonaromatic mono- or bicyclic heterocycle having up to 3 heteroatoms from the group consisting of S, N and O, which may optionally be attached via a nitrogen atom, and/or cyano, and M is a tri-$(C_1-C_6)$-alkylstannyl group or a boronic acid group, in inert solvents in the presence of palladium catalysts at temperatures of 50–140° C., to give compounds of the formula (XIV)

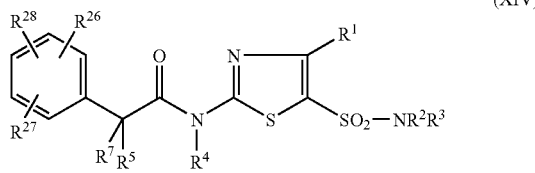

(XIV)

or

[D] compounds of the general formula (XII)

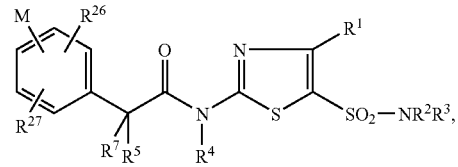

(XII)

in which $R^1$, $R^2$, $R^3$, $R^4$, $R^5$, $R^7$, $R^{26}$ and $R^{27}$ are each as defined above and M is as defined above, are reacted with trifluoromethanesulphonates or halides of the general formula (XIII):

$R^{28}E$ (XIII), in which $R^{28}$ is as defined above and E is as defined above in inert solvents in the presence of palladium catalysts at temperatures of 50–140° C., to give compounds of the formula (XIV).

16. Pharmaceutical composition, comprising a compound of the general formula (I) according to claim 1 in a mixture with a pharmaceutically acceptable carrier or excipient.

17. A method of treating viral infection, comprising administering to a human or animal an effective amount of a compound of the general formula (I) according to claim 1.

18. The method of claim 17, wherein said viral infection is caused by herpes viruses.

19. The method of claim 17, wherein said viral infection is caused by Herpes simplex viruses.

* * * * *

UNITED STATES PATENT AND TRADEMARK OFFICE
CERTIFICATE OF CORRECTION

| | |
|---|---|
| PATENT NO. | : 7,105,553 B2 |
| APPLICATION NO. | : 10/168197 |
| DATED | : September 12, 2006 |
| INVENTOR(S) | : Rüdiger Fischer et al. |

Page 1 of 1

It is certified that error appears in the above-identified patent and that said Letters Patent is hereby corrected as shown below:

On the title page, item (30) Foreign Application Priority Data should read as follows:

(30)     Foreign Application Priority Data
    Dec. 23, 1999 (DE) ....................... 199 62 532
--Aug. 11, 2000 (DE) ........................ 100 39 265.2--

Signed and Sealed this

Twenty-ninth Day of April, 2008

JON W. DUDAS
*Director of the United States Patent and Trademark Office*